(12) United States Patent
Desai

(10) Patent No.: US 6,231,591 B1
(45) Date of Patent: May 15, 2001

(54) METHOD OF LOCALIZED FLUID THERAPY

(75) Inventor: Ashvin H. Desai, San Jose, CA (US)

(73) Assignee: 2000 InjecTx, Inc., San Jose, CA (US)

( * ) Notice: Subject to any disclaimer, the term of this patent is extended or adjusted under 35 U.S.C. 154(b) by 0 days.

(21) Appl. No.: 09/105,896

(22) Filed: Jun. 26, 1998

Related U.S. Application Data

(63) Continuation-in-part of application No. 08/639,199, filed on Apr. 26, 1996, now Pat. No. 5,861,002, which is a continuation-in-part of application No. 08/259,712, filed on Jun. 14, 1994, now Pat. No. 5,562,703, which is a continuation-in-part of application No. 08/025,003, filed on Mar. 2, 1993, now abandoned, which is a continuation of application No. 07/779,108, filed on Oct. 18, 1991, now Pat. No. 5,322,503.

(51) Int. Cl.$^7$ ............................................ A61B 17/50
(52) U.S. Cl. ...................................... 606/210; 604/8
(58) Field of Search ............................ 606/210, 211; 604/8, 9, 10

(56) References Cited

U.S. PATENT DOCUMENTS

| | | | |
|---|---|---|---|
| 557,589 | 7/1896 | Lockwood | 251/349 |
| 1,314,855 | 9/1919 | Carpenter | 604/33 |
| 2,706,660 | 4/1955 | Johnson et al. | 251/348 |
| 3,605,744 | 9/1971 | Dwyer | 604/139 |
| 3,828,780 | 8/1974 | Morrison . | |
| 3,850,175 | 11/1974 | Inglesias | 606/46 |
| 3,948,259 | * 4/1976 | Bolduc | 128/235 |
| 4,402,310 | 9/1983 | Kimura | 604/30 |
| 4,565,200 | 1/1986 | Cosman | 128/642 |
| 4,607,622 | * 8/1986 | Fritch | 128/6 |
| 4,668,215 | 5/1987 | Allgood . | |
| 4,673,393 | 6/1987 | Suzuki et al. | 604/167 |
| 4,760,940 | 8/1988 | Wallace et al. | 251/354 |
| 4,776,840 | 10/1988 | Freitas | 604/33 |
| 4,895,565 | 1/1990 | Hillstead | 604/167 |
| 5,007,908 | 4/1991 | Rydell | 606/47 |
| 5,069,223 | 12/1991 | McRae | 128/734 |
| 5,071,419 | 12/1991 | Rydell et al. | 604/35 |
| 5,073,166 | 12/1991 | Parks | 604/105 |
| 5,125,910 | 6/1992 | Freitas | 604/249 |
| 5,144,961 | 9/1992 | Chan | 608/139 |
| 5,186,714 | 2/1993 | Boudreault et al. | 604/35 |
| 5,188,591 | 2/1993 | Dorsey, III | 604/249 |
| 5,190,541 | 3/1993 | Abele et al. | 604/35 |
| 5,195,958 | 3/1993 | Phillips | 604/33 |
| 5,197,963 | 3/1993 | Parins | 606/41 |
| 5,219,348 | 6/1993 | Buess et al. | 604/40 |
| 5,230,704 | 7/1993 | Moberg et al. | 604/35 |
| 5,244,459 | 9/1993 | Hill | 604/249 |
| 5,247,966 | 9/1993 | Stevens et al. | 604/249 |
| 5,273,524 | 12/1993 | Fox et al. | 604/21 |
| 5,281,218 | 1/1994 | Imran | 606/41 |
| 5,295,956 | 3/1994 | Bales et al. | 604/35 |
| 5,347,990 | 9/1994 | Ebling | 606/139 |
| 5,370,675 | 12/1994 | Edwards et al. | 607/101 |
| 5,385,544 | 1/1995 | Edwards et al. | 604/22 |

\* cited by examiner

Primary Examiner—Michael A. Brown
(74) Attorney, Agent, or Firm—David H. Jaffer; Pillsbury Winthrop LLP

(57) ABSTRACT

A method and apparatus for treating a localized portion of body tissue including an endoscopic surgical instrument including a probe with a canal for guiding a hollow core needle assembly, the assembly having apparatus for extending and retracting a needle relative to the probe. According to the method, the needle is extended into body tissue to deliver a treatment fluid to a localized portion.

28 Claims, 16 Drawing Sheets

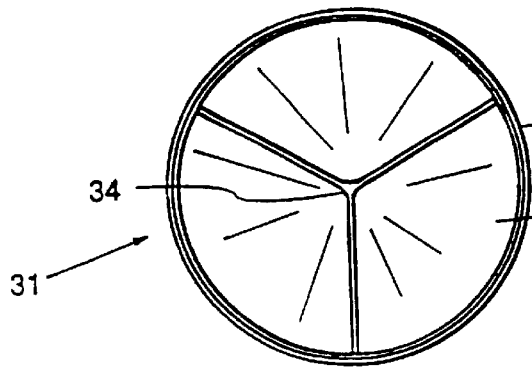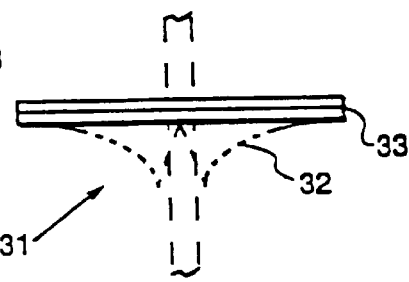
Fig. 3a  Fig. 3b
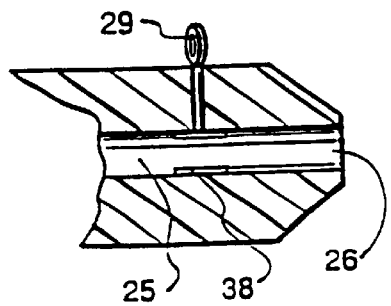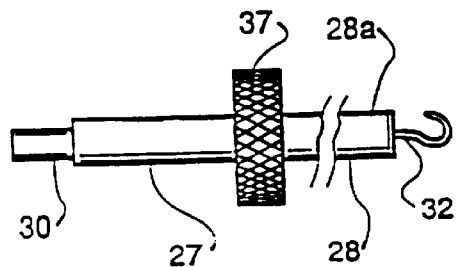
Fig. 4a  Fig. 4b
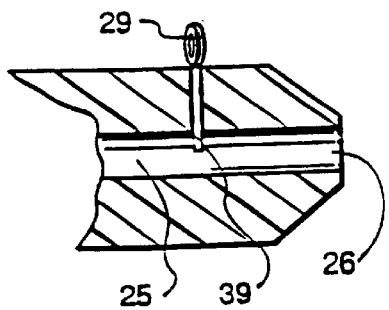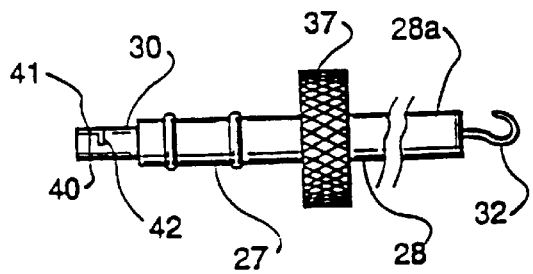
Fig. 5a  Fig. 5b

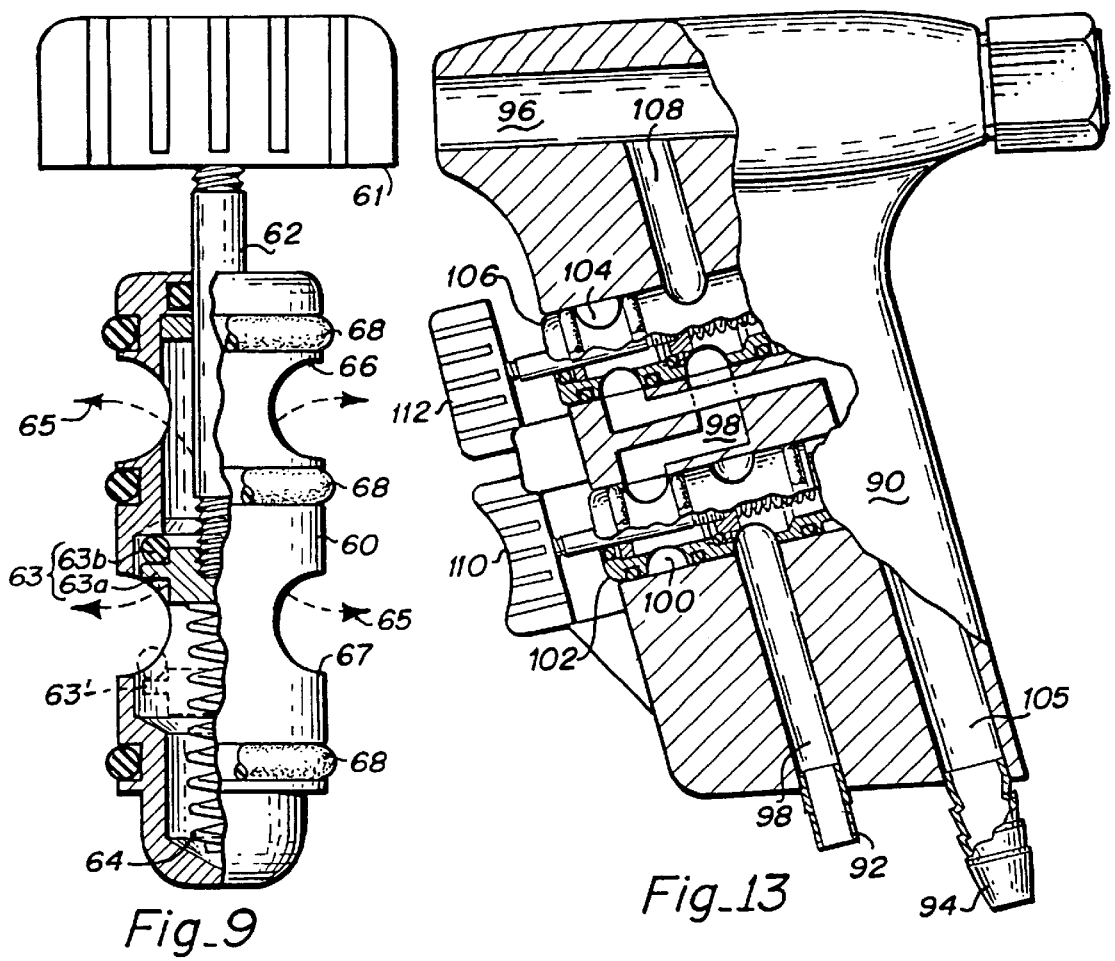
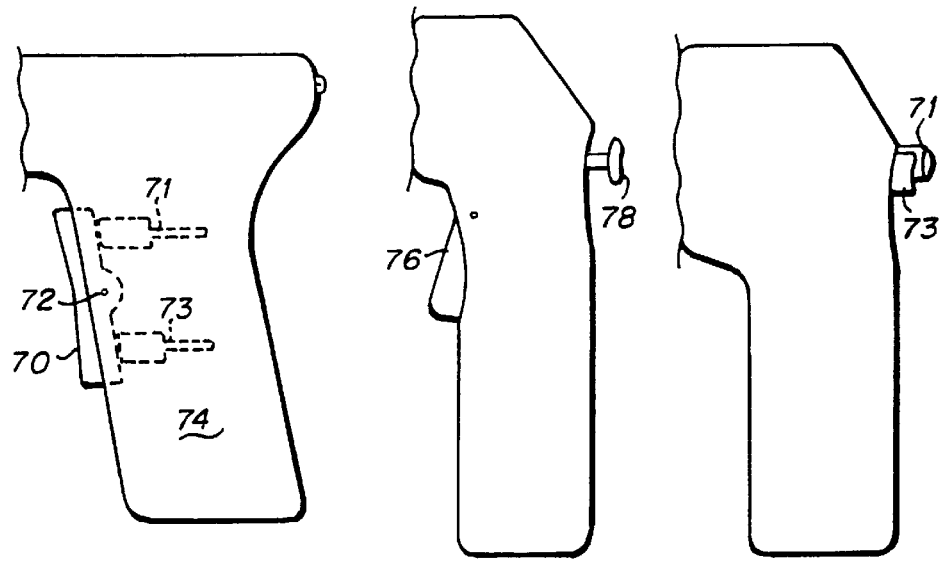

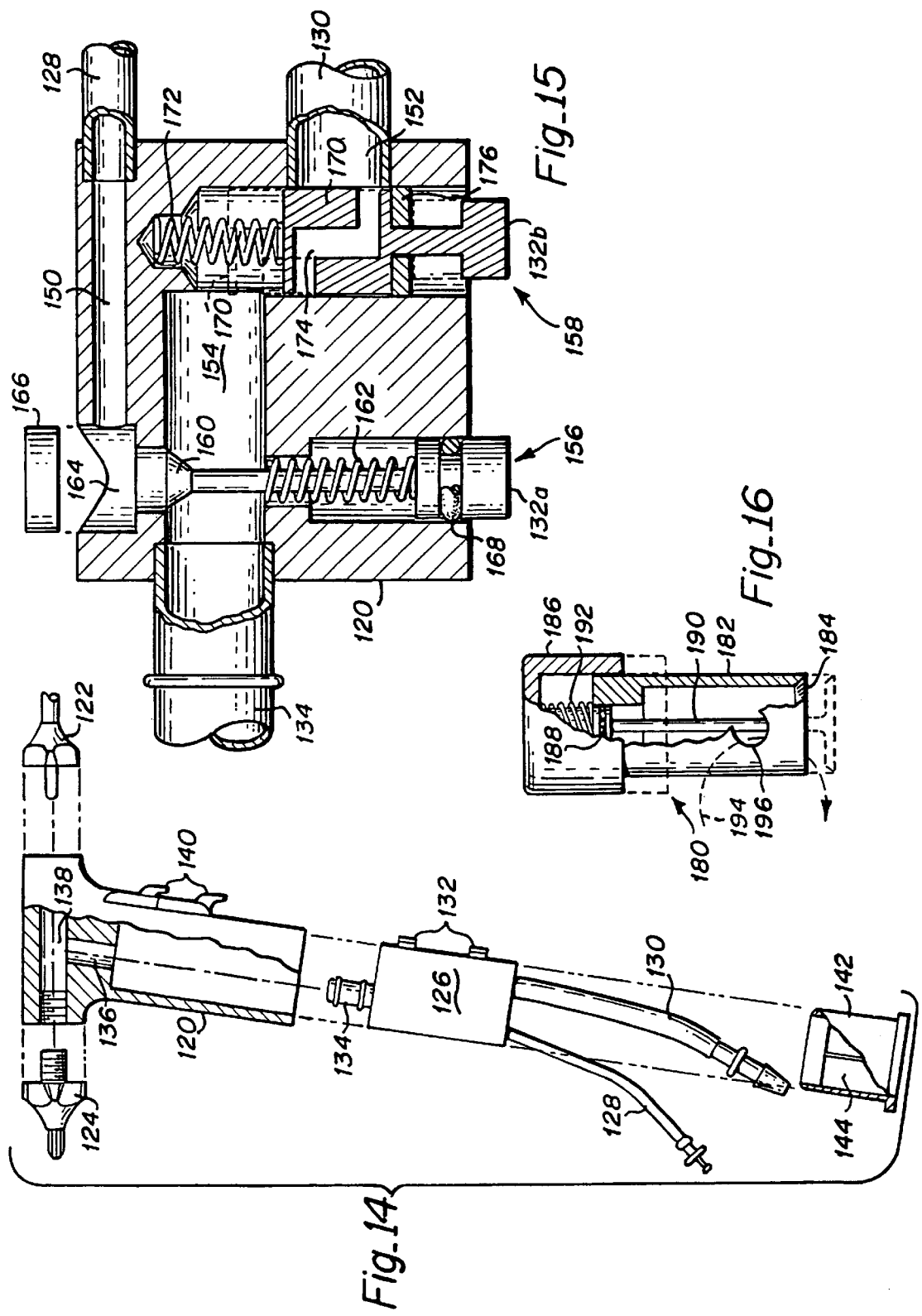

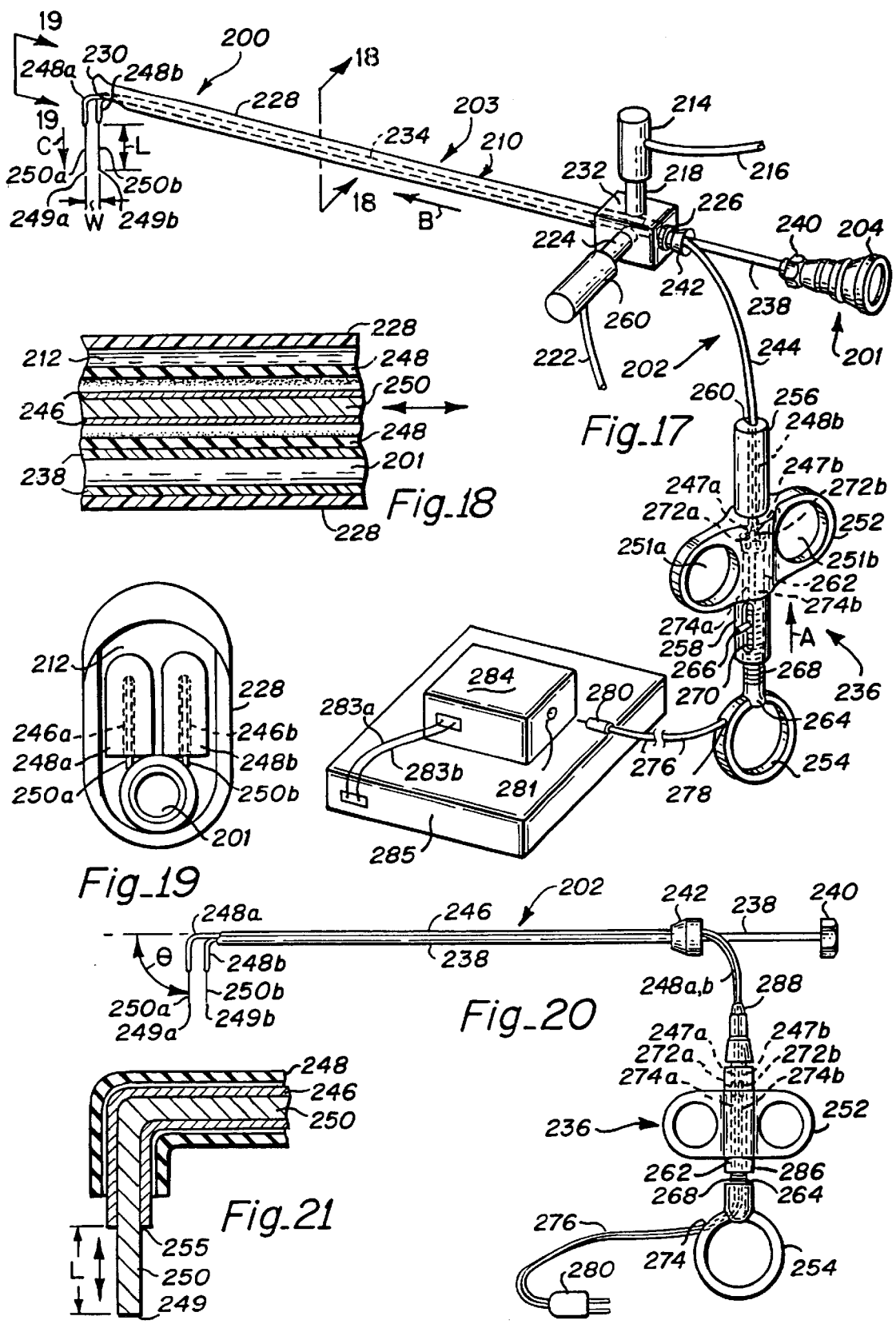

SECTION A-A

THERAPY FLUIDS

- Necrossing agents
  - Ethanol alcohol (1% to 100% pure)
  - Saline solution (.9% to 99%)
  - Acetic acid (1% to 100%)
  - Natural extracts/compounds
  - Enzymes

- Anesthetic agents
  - Lidocaine
  - Markaine
  - Sensorcaine

- Antibiotics

FIG. 29

METHOD OF LOCALIZED FLUID THERAPY

BACKGROUND OF THE INVENTION
RELATED CASES

This application is a continuation in part of U.S. patent application Ser. No. 08/639,199 filed Apr. 26, 1996, now U.S. Pat. No. 5,861,002 which is a continuation-in-part of Ser. No. 08/259,712 (now U.S. Pat. No. 5,562,703) filed Jun. 14, 1994 which is a continuation-in-part of Ser. No. 08/025,003 filed Mar. 2, 1993 (abandoned) which is a continuation-in-part of Ser. No. 07/779,108 filed Oct. 18, 1991 (now U.S. Pat. No. 5,322,503).

BACKGROUND OF THE INVENTION

1. Field of the Invention

This invention relates to a surgical instrument and more particularly to an instrument with the capability for continuous irrigation and evacuation of fluid into and out from a body cavity of a patient during Laparoscopic or Endoscopic surgical procedures, and for the simultaneous measurement of tissue impedance and the ablation of tissue with fixed or retractable electrodes using R.F. energy, and to a method and apparatus for injection of liquids, biomaterial, chemical agents, etc. for performing fluid therapy on interior body parts, and/or insertion of optical fibers of instruments through a hollow core electrode.

2. Brief Description of the Prior Art

Laparoscopic/endoscopic surgical procedure allows a surgeon to see inside the body cavity of a patient without the necessity of large incisions. This reduces the chances of infection and other complications related to large incisions. The endoscope further allows the surgeon to manipulate microsurgical instruments without impeding the surgeon's view of the area under consideration.

During these surgical procedures it is desirable for as few lines as possible to enter the body of the patient. This reduces the size of the incision the surgeon needs to make. It follows from this that the greater the number of functions provided by a single instrument or the greater the number of instruments able to be passed through a single line entering the patient's body, the better.

Furthermore, in certain procedures it may be desirable to irrigate the area under consideration. This in turn necessitates the evacuation of the irrigation fluid or, when bleeding has occurred, the blood or smoke or tissue residue generated by the surgical procedure.

From what has been said above it should be apparent that it is preferable for both irrigation and evacuation to be conducted along a single conduit which, also, acts as an access line for surgical instruments.

A typical device which is used in endoscopic procedures is an electrosurgical probe. Typically such a probe will comprise a radio frequency (i.e. R.F.) energy conductive tube covered with a dielectric material such as polyolefin or Teflon. At one end, for convenience called the operational end, each probe could have any one of a number of functionally shaped monopolar or bipolar electrodes. In addition a probe could have its end formed specifically for irrigation and/or evacuation.

Monopolar and bipolar electrode probes are known in the prior art. Monopolar electrode probes include a single active electrode which is surgically introduced into a body cavity and engagable with and insertable into a tissue portion of the cavity. A passive electrode is attached to the outer body surface of the patient, e.g. typically a conducting plate is adhesively attached to the patient's leg. The body of the patient serves to complete the electrical circuit. Tissue ablation and coagulation is achieved by introducing sufficient power into the active electrode. Bipolar electrode probes include both active and passive electrodes which are similarly introduced together into the body cavity and are spaced apart from each other by a predetermined distance. Each electrode is engageable with and insertable into the tissue portion. Thus, the electrical circuit is completed by the body tissue disposed between the active and the passive electrodes and only the body tissue disposed between the two electrodes get coagulated. Another need that can arise in surgical procedures is for a method and apparatus of application for anesthetics, biomaterial, chemical agents, etc. and other substances to localized areas interior to a patient's body.

Furthermore, any valves controlling the evacuation and irrigation procedures should be constructed so as to minimize the possibility of the valve malfunctions if, for example, any tissue or blood coagulates around their moving parts. Similarly if any of the instrumentation is to be reusable, such instrumentation, including the valves, should be capable of being efficiently cleaned by, for example, flushing.

U.S. Pat. No. 4,668,215 (Allgood) discloses a valve for switching between an evacuation and an irrigation conduit and allowing both such evacuation and irrigation to be done via a single line entering the patient. The mechanism for switching between the irrigation, evacuation and closed configurations is by means of a L-valve or T-valve. This patent, in another embodiment thereof, further provides for a piston valve for making an on-off connection between an evacuation port and the line leading into the patient.

The L- and T-valves have the disadvantage that they must be manipulated by rotation by the surgeon, usually using his/her free hand. The piston valve disclosed in this patent has the disadvantage that it has many areas where blood and tissue accumulation and coagulation can occur which may result in the malfunctioning of the valve. In addition, the piston valve has numerous "dead" areas where fluid flow would not occur. This precludes the device from being effectively cleaned by commonly used flushing techniques. Finally, the Allgood patent does not disclose a single body for housing an evacuation/irrigation control valve together with a housing for laparoscopic and microsurgical instrumentation.

A surgical valve that the applicant is aware of is the piston valve illustrated in FIG. 1 of the accompanying drawings.

In this valve a piston 10 is located within a cylinder 11. The piston 10 can be moved along the bore of the cylinder 11 by means of a plunger 12, from a closed position (as shown) to an open position in which a conduit 13 is aligned with an access port 14. This allows fluid flow along a path to or from access port 14, via conduit 13 and space 16 from or to a further port 15. Upon release of the plunger 12 the piston 10 returns to its closed position under action of a spring 17.

This valve, although easy to use, has the disadvantage that blood and tissue accumulation occurs in space 16 and clogs both the space and the spring 17. This may result in undesirable over-evacuation or irrigation of the patient during surgical procedures.

OBJECTS OF THE INVENTION

It is therefore an object of this invention to provide a surgical instrument which includes control means to allow for the continuous irrigation and evacuation of a body cavity of a patient during microsurgical procedures, with both irrigation and evacuation being performed along a single line into the patient. The instrument should also act as a mounting for electrosurgical probes and microsurgical instruments.

A further object of the invention is to provide a configuration for an instrument which, depending on the material it is constructed of, can be both disposable and non-disposable. In the event that the instrument is "reusable" or "reposable" it is an object of the invention to provide the instrument with conduits, access ports and valves which can easily be cleaned by means of commonly used cleaning techniques and conventional sterilization methods.

It is another object of the invention to provide an electrosurgical instrument with fixed or retractable RF electrodes having the capability to simultaneously perform controlled ablation of tissue using monopolar/bipolar R.F. energy and precise measurement of tissue impedance.

SUMMARY OF THE INVENTION

According to this invention, an endoscopic surgical instrument comprises an irrigation and an evacuation port, each port being connected through independent valves to a single access conduit; a probe connector located at one end of the access conduit, the probe connector being for receiving and retaining a hollow surgical probe; and a monopolar or bipolar radio frequency connector which exits into the access conduit in such a manner so as to make radio frequency connection with a probe received by the probe connector.

Preferably the connector for receiving an end, for convenience called the locating end, of the probe would be in the form of a receiving bore in the access conduit which would include a plurality of O-rings which provide a fluid-tight seal around the locating end of the probe. These O-rings also function to retain the probe in the receiving port while allowing the probe to be rotated. In one embodiment of the invention, the O-rings are, instead of being located within the receiving bore of the access conduit, located about the locating end of the probe.

This invention also provides for a valve, for use as either an evacuation or an irrigation valve, the valve comprising a housing, an activator connected to the housing, at least a first and a second valve access conduit, both of which exit into the housing and a fluid impervious seal mounted within the housing such that activation of the activator causes the first valve conduit to move axially relative to the seal and the second valve conduit such that the seal is disengaged and the conduits are placed in direct fluid communication with each other.

Typically, the instrument of the invention would contain two of the above described valves. One valve would act as an evacuator control while the other valve would act as an irrigation control. Both valves communicate into a single access conduit which, when the instrument is in use, continuously flows into the patient via the receiving bore and the hollow interior of the electrostatic probe.

Preferably the endoscopic surgical instrument of the invention is in the form of a pistol with the "barrel" portion thereof having, at one end thereof, the receiving bore for the locating end of the endoscopic probe and, at the other end thereof, the access port for the microsurgical instruments and endoscopes.

The valves for controlling the evacuation and irrigation procedures may be mounted in the "handle" portion of the pistol-shaped instrument. The valves may be mounted alongside one another in the handle portion and may protrude therefrom to allow finger control by the surgeon using the instrument.

In one alternate embodiment of the invention the surgical instrument includes a housing, a single access conduit formed in the housing, an irrigation port and an evacuation port, each port being connected through independent valves to the single access conduit. The single access conduit has a first end, and a second end which is terminated in an aperture formed in the housing. A closure is provided for the aperture. A viewing device, such as an endoscope, is insertable through the aperture and into the single access conduit. The viewing device is of sufficient length such that it is extendable slightly beyond the first end. A retractable electrode assembly is also insertable through the aperture and into the single access conduit, and is of sufficient length such that it, too, is extendable beyond the first end. The retractable electrode assembly, in one embodiment, includes two retractable RF electrodes spaced apart by a predetermined width. Each RF electrode is made from a superelastic material, e.g. typically Nickel-Titanium (NiTi) metal, is sheathed within a guiding sheath, and is slidable within the sheath such that it is extendable beyond and retractable completely within the sheath. Also, each electrode is connected to a mechanism, operable by a surgeon, for moving the electrode within the sheath. Each electrode is extendable beyond its guiding sheath by a variable length and at a predetermined angle from a longitudinal axis of the single access conduit. Further, each electrode is electrically communicative with means for supplying R.F. energy and means for measuring impedance continuously on a realtime basis. Another embodiment of the invention includes a hollow core electrode through which liquids such as anesthetics, chemical agents, biomaterial, etc. and/or other treatment can be injected/inserted to localized areas within a patient's body. The hollow core can also be used to insert an optics fiber or microsurgical instruments.

These and other objects and advantages of the present invention will no doubt become apparent to those skilled in the art after having read the following detailed description of the preferred embodiment which is illustrated in the several figures of the drawing.

IN THE DRAWINGS

In the following drawings:

FIG. 3a is an illustration of a tricuspid valved access port illustrated in a plan view;

FIG. 3b is an elevation view of a tricuspid valved access port;

FIG. 4a is a section through a receiving bore of the instrument illustrating one way of locating a probe in the bore;

FIG. 4b illustrates the probe referred to in the description of FIG. 4a;

FIG. 5a is a section through a similar receiving bore showing a different way of locating a probe in the bore;

FIG. 5b illustrates the probe referred to in the description of FIG. 5a;

FIG. 9 is a partial section through a different type of valve also suitable for use in the instrument of the invention;

FIGS. 10, 11, 12 and 13 are diagrammatic illustrations showing various configurations of valve operating buttons and triggers;

FIG. 14 is an exploded view of an alternative embodiment of the surgical instrument of the invention illustrating a disposable valve cartridge;

FIG. 15 is a cross section through the disposable valve cartridge illustrated in FIG. 14;

FIG. 16 is a partially sectioned view of another type of valve which can be used in the surgical instrument of the invention;

FIG. 17 is a perspective view of an alternate embodiment of the endoscopic surgical instrument having generally similar valves, as illustrated in FIGS. 7–8, and a retractable electrode assembly having bipolar RF electrodes in electrical communication with a R.F. energy source and a tissue impedance monitoring device;

FIG. 18 is a partial sectional view taken along the line 18—18 of FIG. 17;

FIG. 19 is a view taken along the line 19—19 of FIG. 17;

FIG. 20 is a side elevation view of the retractable electrode assembly shown in FIG. 17;

FIG. 21 is an enlarged view of the tip of the retractable electrode assembly shown in FIG. 17;

FIG. 29 is a list of liquids for fluid therapy;

DETAILED DESCRIPTION OF PREFERRED EMBODIMENTS

Figure 1:
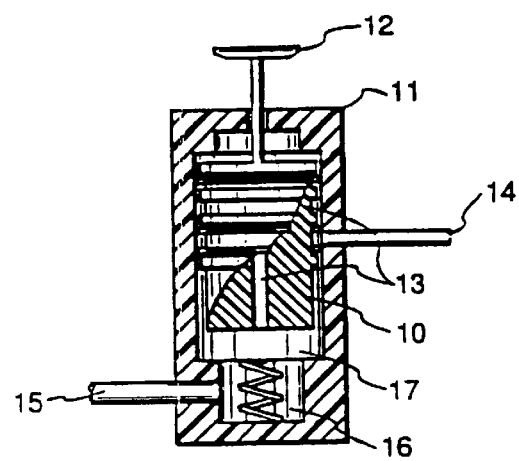
FIG. 1 is a partial sectional elevation through a prior art piston valve.
Figure 2:
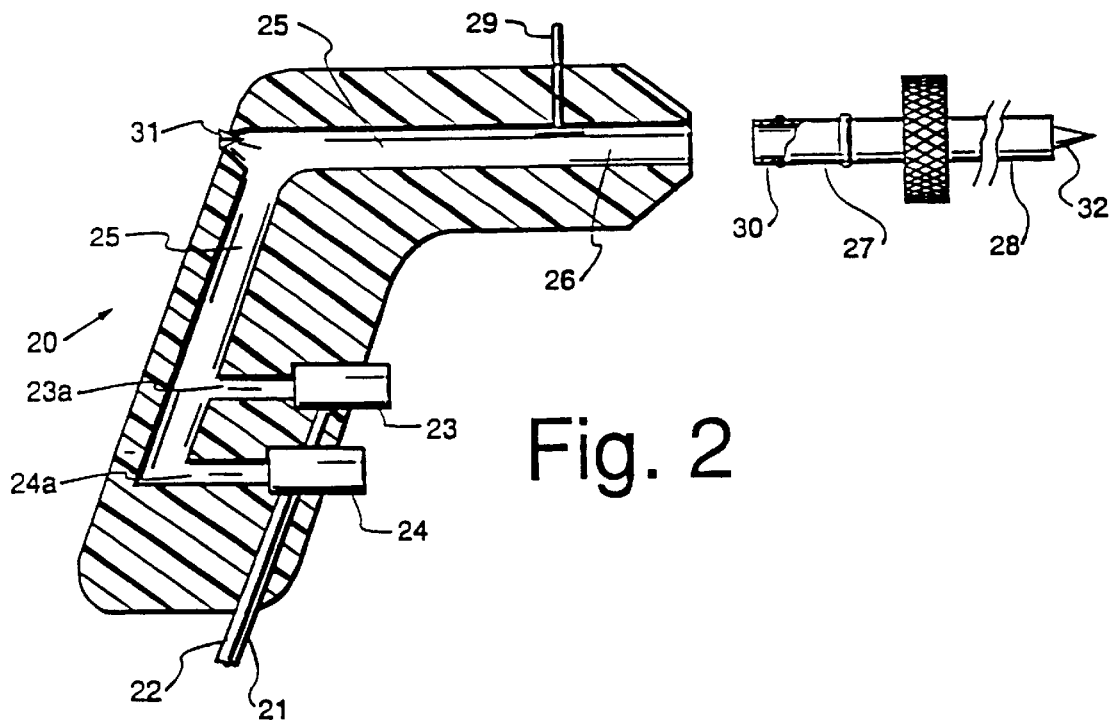
FIG. 2 is a diagrammatic section through a semi-exploded elevation of one embodiment of the endoscopic surgical instrument of the invention.

In FIG. 2 of the accompanying drawings, the endoscopic surgical instrument of the invention is generally indicated as 20. The instrument 20 is shown to include an irrigation port 21 and an evacuation port 22. Each port, 21 and 22, is connected through independent valves 23 and 24, respectively, to a single access conduit 25. The connection between the valves 23 and 24 and conduit 25 is along connector tubes 23a and 24a.

The access conduit 25 leads from the valves and their respective valve conduits to a probe connector 26. This probe connector 26 is designed to receive one end, the locating end 27, of a surgical probe 28 which would be used during microsurgical procedures. The connector 26 is described in more detail with reference to FIGS. 4 and 5 hereafter.

At or near the probe connector 26, a monopolar/bipolar radio frequency connector 29 is located. As illustrated, this is in the form of a R.F. connector. The advantage of a R.F. connector is that it is an industry standard and can be used for connecting the instrument 20 to standard R.F. energy sources marketed by a number of different manufacturers.

The radio frequency connector 29 exits into the access conduit 25 where it makes connection with a point 30, on the locating end 27 of a probe 28 received by the probe connector 26.

The surgical instrument 20 also includes a port 31 which allows the surgeon to insert microsurgical instrumentation and viewing devices along the access conduit 25 and the bore of the hollow probe 28 to exit from the end 32 thereof. The port 31 should provide a fluid-tight seal when no microsurgical instrumentation is being used with the surgical instrument 20. This will prevent fluid, which may be moving along the access conduit 25 to or from the patient, from leaking.

Typically, the access port 31 is in the form of a commercially available tricuspid valve as illustrated in FIGS. 3(a) and (b). In these figures, the valve 31 is shown as being constituted by three segments 35 which in plan view are wedge-shaped and which together form the disc shaped sealing portion of the valve. The segments 35 are held together by means of a circumferential ring 33 which biases the three segments 35 together to form a fluid-tight seal. In use, the microsurgical instrumentation are inserted through the valve at a point 34 where the apexes of the segments 35 come together. This insertion forces the elements of the valve apart to allow ingress of the microsurgical instrumentation. The effect thereof is shown in broken lines in FIG. 3(b). When the instrumentation is removed from the valve 31, the segments 35 are pulled together to form the seal.

In FIG. 4a the probe connector 26 is shown to be constituted by a receiving bore which is coaxial with the fluid access conduit 25. In practice, the diameter of this bore would be the same as that of the access conduit 25 and would be sized to receive the locating end 27 (FIG. 4b) of the probe 28 in a relatively close fit. Within the bore forming the probe connector, a plurality, typically two, O-rings 36 are located. When the locating end 27 is inserted into the bore 26 these O-rings provide a snug, fluid-tight seal about the end 27. Once the locating end 27 of the probe is received within the bore 26 it is capable of being rotated about its longitudinal axis, by means of a knurled rotation knob 37 located between the locating end 27 and the operational end 32 of the probe 28.

The probe 28 would typically be made of a electrostatic conductive material coated with a non-conductive material such as heat shrink polyolefin or Teflon. Electrostatic/radio frequency energy is passed along the probe 28 from the radio frequency connector 29 via electrostatically conductive plates 38 located within the bore of the probe connector 26 and onto the end 30 of the probe 28. The end 30 is so designed such that when the locating end 27 of the probe is received by the probe connector 26, electrostatic connection is made between the plate 38 and the connector 30. This allows the surgeon to pass energy into the patient being operated on.

An alternative radio frequency connector is illustrated in FIGS. 5a and 5b. In this case, the R.F. connector 29 exits into the bore 26 in the form of a pin 39. In the conductive end 30 of the probe 28 an L-shaped slot 40 is formed. As the probe 28 is inserted into the receiving bore 26, the pin 39 engages the axially-orientated leg 41 of the L-shaped slot 40. When the probe can be inserted no further along the bore it is twisted, in this case in an anti-clockwise direction, such that the pin 39 and the axially transverse leg 42 of the L-shaped slot 40 engage each other to lock the probe 28 into position. In this embodiment the probe 28 cannot be rotated by means of the knurled knob 37.

FIG. 5b further illustrates an alternative positioning of the O-rings 36. In this case they are located on the locating end 27 of the probe 28.

From FIGS. 4 and 5, although not shown, it will be apparent that the diameter of the operational shank 28a of the probe 28 can be variable. Typically, the probe, as shown, would have a diameter of 5 mm. This diameter can, however, be increased to 10 mm which would be close to the diameter of the locating end 27 of the probe, as well as that of the internal bore diameter of the access conduit 25. The advantage of 10 mm diameter probes is that the evacuation of removed tissue and objects such as the gall-stones can be more effectively achieved. Obviously, when the bore of the operating shank 28a of the probe, the locating end 27 and the access conduit 25 are all 10 mm in diameter, the diameter of the evacuation port 22 and its related valve 24 and connector tube 24a must also be 10 mm.

In FIG. 6(a) to (i), side views of a number of different electrode shapes are illustrated. It will be appreciated that the electrode tips could be either monopolar or bipolar. In the case of bipolar electrodes, only one electrode is illustrated since a second electrode is fully obscured by the visible electrode. These electrode tips would be located on the operating end of the probe 28.

As can be seen from the figure, a number of the tips are not symmetrical about the longitudinal axis of the probe 28. It is for this reason that it is desirable for the probe 28 to be mounted on the instrument in such a manner to allow for a rotation of the probe about its longitudinal axis. As has been previously indicated, this will give the surgeon the opportunity of rotating any non-symmetrical tips, inside the patient, without having to rotate his or her wrist.

Figure 6:
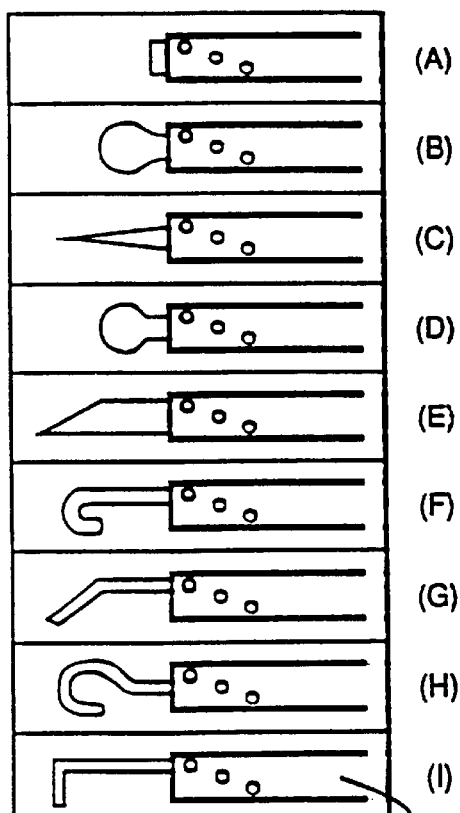
FIG. 6 is a side view illustrating in (a)–(i) various electrostatic probe operational ends.

This invention extends also to an electrostatic probe 28, substantially as described in any of the FIGS. 4 to 6.

Figure 7:
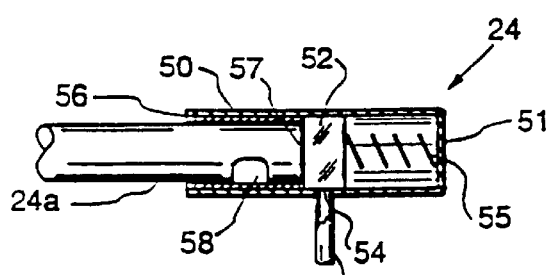
FIG. 7 is a section through a valve according to the invention with the valve being in the shut position.
Figure 8:
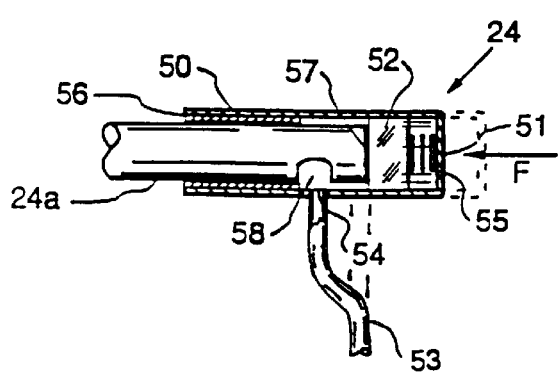
FIG. 8 is the valve of FIG. 7 in the open position.

The details of one type of irrigation/evacuation valve are illustrated in FIGS. 7 and 8. The valve 24 indicated in both figures comprises a housing constituted by a hollow tube 50 and an activator in the form of a button 51 formed integrally with the tube 50. A fluid impervious seal 52 is located within the tube 50. Referring specifically to FIG. 7, in which the valve is shown in the shut position, it can be seen that the seal 52 lies between a first valve conduit 53 which leads to the evacuation port 22 (not shown) and a second valve conduit in the form of connector tube 24a which leads into the primary access conduit 25 of the surgical instrument. In effect, the seal 52 prevents the conduits 53 and 24a from being in communication with each other.

The first valve conduit 53 is mounted onto the wall of the tube 50 and opens into the interior of the tube 50 through a hole 54. Between the seal 52 and the button portion 51 of a tube 50, a spring 55 is located. On the side of the seal 52, opposite to which the spring is located, a tubular insert 56 is located. This tubular insert has a snug but slidable fit over the outer wall of the second valve conduit 24a as well as a tight, fluid impervious fit into the inner bore of the tube 50. This tube 56 acts as a stop which prevents the spring 55 from pushing the seal 52 out of the hollow tube 50.

To open the valve, as is illustrated in FIG. 8, an activating force, applied along a line F to the button 51, will cause the button to move from the position indicated in broken lines to the illustrated open-valve position. As the button moves, so does the hollow tube 50, taking the first valve conduit 53 along with it. In addition, the leading edge 57 of the second valve conduit 24a bears against the seal 52 causing the seal to move relatively to the tube 50. This in turn disengages the seal from sealing the hole 54 in the wall of the tube 50. The movement of the first valve conduit 53, relative to the second valve conduit 24a, places the respective openings 54 and 58 of these two conduits in fluid communication with each other thereby allowing an unobstructed fluid flow along both access conduits.

Upon release of the force on the button 51, the bias of the spring 55 will return the valve to its shut position.

It is evident from the construction of the valves illustrated in FIGS. 7 and 8 that they can be readily cleaned by commonly used cleaning such as flushing. In addition, the valves have almost no areas where blood and tissue accumulation and coagulation can occur, and if such accumulation and coagulation does occur the valves cannot be jammed in the open position. This is because the spring biasing the valve into its closed position is located in an effectively sealed area. Furthermore these valves have been tested to a pressure of up to 100 psi without the integrity of the valve seal being adversely affected.

An alternative form of valve, to that illustrated in FIGS. 7 and 8 above, is shown in FIG. 9. In the figure the valve is shown to include a generally cylindrical valve body 60, an activating button 61 and a plunger 62. A hollow bore runs down the center of the valve body 60 and contains the valve seal 63. The valve seal 63 is made up of a circular washer 63a and a sealing O-ring 63b and is screwed onto the bottom of plunger 62. The valve seal 63 is biased into its illustrated sealing position by means of a spring 64 located in the bottom part of the valve body 60.

To open the valve, the button 61 is depressed so that the plunger 62 forces the valve seal 63 downwards against the bias of the spring 64 to a position shown in broken lines 63', in the figure. As a result, a fluid path, indicated by arrows 65, is opened between an upper pair of cutouts 66 and a lower pair of cutouts 67. Each pair of cutouts opens into the hollow bore in the center of the valve body 60 and, when this valve is inserted into the surgical instrument, into either an evacuation or irrigation conduit. Closure of the valve is achieved by releasing the button and allowing the spring 64 to return the valve seal 63 to the sealing position.

One advantage of this embodiment of the valve is that it is easily removed from and inserted into the surgical instrument of the invention. Accordingly the valve can easily be removed for cleaning or disposal and replacement. This is further illustrated below with respect to FIG. 13. It is sufficient here to mention only that the surgical instrument is provided with a receiving bore for each valve and that the valve includes a plurality (in this case 3) O-rings 68 which, when the valve is inserted into its respective receiving bore, provide a number of fluid tight seals against the inside of the bore.

Either of the two types of valve described in FIGS. 7 to 9 can be used on the instrument 20. Typically one valve would act as an evacuation valve while the other as an irrigation valve. Different types of arrangements of valves and valve activation means are illustrated in the following 4 figures.

One way of activating the valve is by means of a rocker-shaped trigger 70 illustrated in FIG. 10. The trigger 70 is pivotally mounted on a point 72 on the handle 74 of the pistol. Depressing the trigger 70 to operate the irrigation valve 71 would not interfere with the operation of the evacuation valve 73. Similarly, operation of the trigger 70 to operate the evacuation valve 73 would in no way effect the operation of the irrigation valve.

In FIG. 11 a trigger mechanism 76 is shown for operation of only one of the buttons. The other button 78 would be located for operation by means of the surgeon's thumb in a position removed from the trigger 76. This could, for example, be near the top end of the handle portion of the instrument.

Yet a further positioning of the buttons 71 and 73 is indicated in FIG. 12. In this instance, the buttons protrude from the top rear of the pistol handle and are located side-byside. To prevent confusion between evacuation and irrigation procedures, the tops of the buttons have different shapes. So, for example, the button to manipulate the evacuation valve could be concave while the button for manipulating the irrigation valve could be convexly shaped.

FIG. 13 illustrates still another arrangement of buttons and valves, in this case an arrangement particularly suited to the valve shown in FIG. 9.

In this figure only the pistol grip 90 of the surgical instrument of the invention is shown. An irrigation port 92 and evacuation port 94 enter the pistol grip 90 at the bottom of its handle portion. The ports 92, 94 are, in use, respectively connected to irrigation and evacuation conduits (not shown) and, to this end, suitable connectors, as illustrated, are provided.

The irrigation port 92 communicates with the main access conduit 96 (referenced as 25 in FIGS. 2, 4 and 5) along an irrigation conduit 98 which extends from the irrigation port 92 and into the rear of the bore 100 which houses an irrigation valve 102. From there it extends along the bore 100 to a point near the front of the bore from where it exits into the body of the grip 9C to enter rear of the bore 104 which houses an evacuation valve 106. the irrigation conduit extends directly across the bore 104 at this point and becomes a central conduit 108 which communicates with the access conduit.

On the other hand, the evacuation port 94 communicates with an evacuation conduit 105 which extends along the pistol grip 90 directly into the front of the bore 104, down to the bore 104 to its rear from where it exits into the central conduit 108.

In the position shown, both the irrigation and evacuation valves 102, 106 respectively, are shown in the off or shut configurations and neither evacuation or irrigation can take place. Should irrigation of the patient be required, the dish-shaped irrigation button 110 is depressed and the valve 102 opens (ie. its valve seat moves to the right in the drawing) to allow irrigation fluid to pass along the irrigation conduit 98 and into the bore 104. In this bore 104 the evacuation valve 106 is in the off configuration. However, a fluid path exists across the pair of cutouts (67 in FIG. 9) and therefore the irrigation fluid can pass through the body of the valve 106 and into the central conduit 108 and, from there, into the access conduit 96.

When evacuation is desired the irrigation button 110 is released and the spring associated with the irrigation valve 102 biases it into the shut or off configuration. Thereafter the flat topped evacuation button 112 is depressed to open the evacuation valve 106. This allows the patient to be evacuated along the main access conduit 96, into the central conduit 108, then from the rear to the front of the bore 104 and, from there, out along the evacuation conduit 105.

As has been indicated earlier, the valves 102, 106 are easily inserted into and removed from their respective bores 100, 104. This allows the pistol grip 90 (which is typically stainless steel and is reusable) to be cleaned efficiently. The valves, typically being of plastic and being difficult to clean, can be discarded and replaced with new valves.

A variation on this theme of discardable valves is illustrated in FIG. 14. In this figure the surgical instrument is shown to include a pistol grip 120, a surgical probe 122, which can be screwed into the front of the pistol grip 120 and a radio frequency connector 124 which screws into the back of the grip 120.

The instrument also includes a removable (and disposable) valve cartridge 126. The cartridge 126 includes an irrigation pipe 128 and an evacuation pipe 130 both of which are individually operated by valves (as will be further illustrated in FIG. 15) under action of button-shaped actuators 132. Both the irrigation and evacuation pipes communicate into a single conduit (not shown) which runs down the center of a male connector fitting 134. Where the cartridge 126 is inserted into the grip 120 the connector 134 fits into the base of a central conduit 136 which, in turn, opens up into the main access conduit 138 of the instrument. When the cartridge 126 is located in the grip 120 the actuators 132 are located directly below a pair of operating triggers 140 which can be used to operate the irrigation/evacuation procedures described before.

Finally, when the cartridge 126 is in place, it is held there by means of a retainer clip 142 which clips in behind the cartridge 126. The retainer clip 142 has apertures 144 formed in it to allow the irrigation and evacuation pipes 128, 130 to pass through it.

Although it will be apparent that the valve types described above are also suitable for use in the cartridge 126, a further valve configuration is illustrated in FIG. 15, which illustrates the cartridge 126 in greater detail.

In this figure, the cartridge 126 is shown to include an. irrigation conduit 150 and an evacuation conduit 152, both of which lead to a central access conduit 154 which extends down the center of the male connector 134. Irrigation and evacuation procedures are controlled by irrigation and evacuation valves 156 and 158, respectively.

The irrigation valve 156 consists of a valve seal 160 mounted onto a stem which is screwed into an activator button 132a. A fluid tight seal is provided for the valve 156 by an O-ring 168 mounted onto the cap 132a. The valve seal 160 seals against a valve seat, formed at the junction between the irrigation conduit 150 and the central access conduit 154 and is held in the sealing position (as shown) by a spring 162.

Access to the valve seat is through a hole 164 formed into the top (as shown in the drawing) of the cartridge 126. This hole 164 can be closed off with a cap 166 and allows the irrigation valve 156 to be inserted into the cartridge 126. This is done by inserting the valve seal 160 and its associated stem into the hole 164 from above and inserting the spring 162 from below. Thereafter the cap 132a can be screwed onto the stem to hold the entire valve 156 in place.

To operate an irrigation procedure the button 132a is depressed to move the valve seal 160 clear of its seal to open a fluid path between the irrigation conduit and the central access conduit. Releasing the button 132a causes the spring 162 to force the seal 160 back into its seat thereby automatically shutting the valve.

The evacuation valve 158 is of a different construction. In this valve 158, the valve seal 170, in its off position as shown, seals the mouth of the evacuation conduit 152.

In operation, the seal 170 is moved under action of a plunger and evacuation button 132b from the position shown to a position 170' in which an end of a conduit 174, formed through the seal 170, aligns with the central access conduit 154. At the same time the other end of the conduit 174 is aligned with the evacuation conduit 152 and evacuation can be accomplished. By releasing the button 132b, the spring 172 biases the seal 170 back into its sealing position.

Assembly of this evacuation valve 158 is by inserting the entire valve mechanism into its valve bore and sealing a collar 176 in the bore.

As has been indicated with reference to FIG. 14, the cartridge 126 is of the disposable type and is intended for use only once. Accordingly the considerations of valve flushing (during cleaning) are not entirely applicable here.

In FIGS. 16 yet another type of valve, which can be used as either an irrigation or an evacuation valve, is illustrated.

The valve, generally indicated as 180, is shown to include a hollow cylindrical valve body 182 which is sealed at its lower end by a valve seal 184 and at the other by an activator button 186. The activator button 186 seals against the valve body with an O-ring 188 and is connected to the valve seal 184 by means of a plunger 190.

To open the valve 180, the button 186 is depressed against the bias of a spring 192 to move the valve seal 184 to the position indicated in broken lines. This opens a fluid path 194 between an opening 196 formed in the sidewall of the valve body and its lower end. Releasing the button 186 allows the spring 192 to force the seal 184 back into the closed position.

One advantage of this valve is that it is very simple and inexpensive to manufacture and can, therefore, readily be disposed of.

Finally, it will be apparent to anyone skilled in the art, that the surgical instrument of this invention could be made from any suitable material. In the event that the instrument is intended for single use, plastic material could be used. Alternatively, for reusable or reposable instrument, the instrument can be made of a more durable material.

FIG. 17 is a perspective view of an endoscopic surgical instrument 200 which is an alternate embodiment of the surgical instrument 20 described above. FIG. 18 is a partial sectional view of a portion of the instrument 200 taken along the line 18—18 of FIG. 17 and FIG. 19 is another view of the instrument 200 taken as indicated by the line 19-19 of FIG. 17. FIG. 20 illustrates the retractable electrode assembly 202. When viewed together, FIGS. 17–20, illustrate the instrument 200 including an endoscopic instrument 201, a retractable RF electrode assembly 202, an continuous irrigation and evacuation assembly 203, a R.F. energy source 285, and a tissue impedance monitoring device 284. It will be appreciated that, although two retractable RF electrodes are illustrated and subsequently described, in alternate embodiments the retractable electrode assembly could have one or more than two retractable RF electrodes. Also, although a bipolar retractable RF electrode assembly is illustrated and subsequently described, it will be appreciated that a monopolar retractable RF electrode assembly could be used.

The assembly 203 includes a housing 210, an irrigation valve assembly 214, and an evacuation valve assembly 220. The housing 210 includes an elongated portion 228 having a generally oval cross section. The portion 228 includes a free tip end 230 and a secured end which is attached to a handle portion 232. The portion 232 is held by the surgeon, and the portion 228 is surgically introduced into a body cavity (not shown) of the patient. A single access conduit 212 (a portion of which is best seen in FIGS. 18 and 19) is formed between an inner surface of the portion 228 and the objects carried within the portion 228. The conduit 212 is disposed along the entire longitudinal length of the portion 228 and is functionally similar to the conduit 25 (FIG. 2) in that it permits the irrigation and evacuation of fluids into and out from the body cavity into which the portion 228 is inserted. The conduit 212 is open at the tip end 230 and can be accessed, at its opposite end, via an aperture and associated closure 226 formed in the handle portion 232. The closure 226 is in the form of a tricuspid valve and is substantially similar to the valve 31 illustrated and described above (FIG. 2).

The irrigation valve and the evacuation valve assemblies 214, 220 are substantially similar to the irrigation and evacuation valves 23, 24 described above (FIG. 2). The valve assemblies 214, 220 operate in a similar manner to valves 23, 24 (FIGS. 7, 8). Depressing the valve assemblies 214 or 220 permits the communication of fluid in a valve first conduit 216 (or 222) with a valve second conduit 218 (or 224). Each of the valve second conduits 218 and 224 are in fluid communication with the conduit 212 (in the same manner that the conduits 23a, 24a are in fluid communication with the conduit 25, FIG. 2). Thus, when the valve assembly 214 is operated, irrigation fluid can be communicated to the conduit 212 and out through the tip end 230, and delivered to the body cavity. In a similar manner, fluids in the body cavity can be evacuated if the valve assembly 220 is operated.

The retractable electrode assembly 202 includes a means for guiding the angular orientation of the electrode or guide sheath 248, an endoscope sheath 238, a electrode movement mechanism 236, a tissue impedance measurement device 284, and a R.F. energy source 285. The sheath 248 is generally parallel to the scope sheath 238. The sheath 248 and the sheath 238 are each insertable into an opening of an insert flange 242, into the aperture of the handle portion 232 of the assembly 203. The sheath 248 and the sheath 238 are insertable within the conduit 212 and are each of sufficient length such that when each is fully inserted within the conduit 212, each extends slightly beyond the tip end 230 of the cylindrical portion 228.

The endoscopic instrument or endoscope 201 is substantially similar to the endoscope instrument described above, and can be any of a number of devices known in the prior art. An eyepiece 204 is shown attached to the endoscope 201. The endoscope 201 is slid into the scope sheath 238 until the eyepiece 204 engages a flange 240 which is attached to the sheath 238. Thus, the endoscope 201, and the sheath 248 of the retractable electrode assembly 202 are both insertable within the portion 228 of the irrigation and evacuation assembly 203.

Each of two RF electrodes 250a, 250b is sheathed within its respective guide sheath 248a, 248b. Although the illustrated embodiment depicts two RF electrodes, it will be appreciated that the assembly 202 could have one or more than two electrodes. Each electrode 250a, 250b includes a first or distal end 249a, 249b, a second, or proximal end 247a, 247b, and a central portion (not shown) disposedly connected therebetween. A coating of insulation 246 is disposed onto the bare electrode 250. The insulation coating 246 may be in the form of a tube of material (such as teflon) heat shrunk around the bare electrode 250. Alternately, the insulating coat 246 may be powder deposited, using vacuum deposition techniques, onto the bare electrode 250. In either case, nearly the entire length of the bare electrode 250 is covered by the insulating coat 246.

The electrodes 250a, 250b have a generally constant diameter throughout its entire length and are sized such that they can be slid within the sheaths 248a, 248b. That is, there exists a sufficient clearance (e.g. 0.005 inch) between the outside diameter of each of the insulating coats 246a, 246b of the electrodes 250a, 250b and the inner diameter of the respective sheaths 248a, 248b. Each electrode 250a, 250b is made from a superelastic metal material, e.g. typically a Nickel-Titanium (NiTi) metal alloy. The guide sheaths 248a, 248b are made from a rigid plastic or coated metal tubing which forms a rigid conduit that guides, i.e. deforms, the electrode along a predetermined path.

As best seen in FIG. 19, the electrodes 250a, 250b and their respective sheaths 248a, 248b are contained within the cross sectional envelope of the portion 228. Thus, the required incision into the patient need only accommodate the cross sectional area of the portion 228. The presence of the extendable electrodes does not increase the size of the required incision. It should be also noted that each electrode 250a, 250b descends downwardly into the field of view of the endoscope 201. In this manner the surgeon is able to view the extension of each electrode 250a, 250b beyond the end of the sheath 248a, 248b.

The two electrodes 250a, 250b and their respective insulators 246a, 246b are encased within their respective guide sheaths 248a, 248b which are encased within a plastic insulating covering 244. The electrodes 250a and 250b encased within the plastic covering 244 exits the housing 232 through the opening in the flange 242.

Each electrode 250a, 250b is in parallel electrical communication with a tissue impedance measuring device 284 and a R.F. energy source 285. The covering 244 enters the movement mechanism 236 through an opening 260 formed in a sleeve 256 of the mechanism 236. The electrodes 250a, 250b and their respective insulators 246a, 246b exit from the covering 244 and each of the second ends 247a, 247b, of each of the electrodes 250a, 250b are attached to connecting pins 272a, 272b, respectively. The connecting pins 272a, 272b are mounted at an end of a plunger 264.

Each connecting pin 272a, 272b is in communication with a wire 274a, 274b each of which passes through the plunger 264, through an opening 278, and into an insulated line 276 which is terminated in a plug 280 which is matingly engagable with a receptacle 282 of the tissue impedance measuring device 284. The R.F. source 285 is in electrical communication with the impedance measuring device via electrical lines 283a and 283b. The source 285 and the impedance measuring device 284 are connectable in parallel in order to get realtime impedance measurement of tissue engaged between the first ends 249a, 249b of each of the electrode 250a, 250b.

The movement mechanism 236 includes a finger ring portion 252, and a thumb ring portion 254. The finger ring portion 252 is a generally flat plate having finger loops 251a, 251b formed therein. A passage 262 is formed through the finger ring portion 252 such that the longitudinal axis of the passage 262 is disposed between each finger loop and lies coplanar with the plane of each finger loop. The sleeve 256, and a cylinder 258 are partially inserted into opposite ends of the passage 262. The sleeve 256 has a passage longitudinally formed therein so as to receive the covering 244. The cylinder 258 has a passage longitudinally formed therein which is aligned with the passage of the sleeve. The plunger 264 is slidable within the passage of the cylinder 258. One end of the plunger is attached to the thumb ring portion 254, and the connection pins 272a, 272b are mounted to the other end of the plunger 264. The outer surface of the plunger 264 is visible through an access cutout 270 formed in the cylinder 258. In one embodiment, an indicator post 266 is attached to the outer surface of the plunger 264 and passes through the access cutout. 270 to give an immediate visual indication of the position of the plunger 264 within the cylinder 258. In a preferred embodiment, the outer surface of the plunger 264 is scored with a plurality of indicator marks 268 to provide a visual indication of the position of the plunger 264 within the cylinder 258, which corresponds to variable length of extension of each of the electrodes beyond their respective insulating sheaths.

In operation, the irrigation and evacuation valves, and the endoscope operate as described above. Regarding the retractable electrode assembly 202, a free hand of the surgeon is used to operate the movement mechanism 236. The surgeon's fingers are engaged within the finger ring loops and the thumb is engaged within the thumb ring portion. The thumb either pushes or pulls on the thumb ring thereby moving the attached plunger 264 into or out of the cylinder 258 and the passage 262. As the plunger 264 moves each of the first ends 249a, 249b of each of the electrodes 250a, 250b move because the connection pins 272a, 272b mounted to the plunger are attached to each of the second ends 247a, 247b of each of the electrodes 250a, 250b. Thus, as the plunger moves in the direction of the arrow A, the central portions of each of the electrodes moves within their respective insulators in the direction of the arrow B, and the first ends 249a, 249b move in the direction of the arrow C.

FIG. 21 illustrates the first end 249 of the electrode 250. The guide sheath 248 is formed with a bend at one end. The electrode 250 slides within the sheath 248 and exits the sheath 248 under the guidance of the sheath 248. The insulating cover 246 permits the easy sliding of the electrode within the sheath 248. Although a bend of 90 degrees is illustrated, it will be appreciated that a bend of any angle may be formed in the sheath 248 so as to guide the electrode 250 into a variety of angular dispositions. It should be noted that the electrode 250 is bare in the vicinity of the first end 249. A predetermined length value L, measured from the tip of the electrode to the end 255 of the insulating coat 246, represents the length of the electrode 250 that is bare or uncoated. Typical values for L range from 0 to 3 cm.

The first ends of each electrode extends beyond its respective sheath 248 by a length greater than the predetermined extension length L in order to permit the bare electrode to penetrate a tissue portion up to the full L value. Further, the first ends of each needle electrode are separated by a predetermined separation width W (typically 0.1–2.0 cm) and each first end forms a predetermined angle θ with respect to the longitudinal axis of portion 228. In the illustrated embodiment, the angle θ is 90 degrees. Typical values for θ range between 0 and 360 degrees.

During surgical procedures, the tip end 230 of the portion 228 of the instrument 200 is brought adjacent to a target tissue area of the body cavity. The first ends of each electrode are extended beyond their respective sheaths such that each first end is embedded into the soft target tissue area thereby defining a tissue portion engaged between the adjacent first ends of each electrode. The power source is energized and R.F. energy is transmitted from one electrode to the adjacent electrode. The energy transmission causes a coagulation of the tissue portion engaged between the adjacent electrodes and ablation of the target tissue.

Using the present invention, the surgeon can predict and control the amount of tissue ablation/coagulation with greater accuracy and safety. As described above, the spacing between the two parallel first ends of each electrode remains constant at some predetermined W value, e.g. 1.0 cm. Also, the extension of the electrodes beyond the insulators at a given angle, i.e. the depth of penetration of each first ends of each electrode into the soft tissue portion, can be precisely controlled by observing the indicator marks on the plunger. Predictable and precise tissue ablation is therefore possible with the present invention because the depth of each first end of each electrode in soft tissue can be precisely controlled by the surgeon. That is, the surgeon can predict a cylindrical zone of ablation by controlling the depth of the retractable first ends into the soft tissue portion. This precise depth control enables the surgeon to predict the zone of ablation with greater accuracy and safety than prior art non-retractable monopolar RF devices, or prior art laser delivery systems.

The cellular structure of body tissue contains water which is a conductor of electrical energy. Consequently, a portion of body tissue also has an associated resistance or impedance value. In prior art monopolar electrode devices, tissue impedance is difficult to measure. However, in the present invention, precise impedance measurement of the soft tissue in the proximity of the bipolar electrodes is possible. In the present invention, during the tissue coagulation process simultaneous measurement of the impedance of the tissue engaged between the extended first ends of the electrodes signals the completion of the tissue coagulation process and provides assurance and confirmation to the surgeon.

R.F. energy applied to the tissue engaged between the first ends of the two electrodes causes the tissue to coagulate which decreases the water content associated with the tissue. As the water content decreases the conductivity of the tissue decreases. For a constant R.F. energy, as the conductivity decreases the impedance (or resistance) associated with the tissue increases. The tissue impedance is highest when the tissue is completely coagulated, since coagulated tissue has a minimum amount of water content and current flow is blocked from one electrode to the other electrode. However, at the beginning of the ablation procedure, the tissue impedance is at a minimum because the water content of the tissue is at its highest level and the tissue is a good conductor and allows the maximum current to flow from one electrode to the other. During the ablation procedure, as the tissue coagulates the water content decreases and the tissue impedance increases. The tissue impedance measurement device 284 can be designed to transmit an variable frequency audible signal, i.e. a beeping tone, when the tissue impedance is at its lowest value. As more tissue is ablated and as the tissue impedance reaches its highest value the audible signal decreases in frequency. In the present invention, the tissue impedance is monitored or measured on a relative basis. That is, the impedance measured or monitored is the impedance of the tissue engaged between the two needle electrodes.

FIGS. 22A through 22H illustrate alternate electrode configurations. It will be noted that the preferred embodiment of the present invention includes two electrodes with a θ of 90 degrees, and a L value of 0–3 cm, and a W value of 0.1–2.0 cm. It will be appreciated that a variety of electrode configurations, with associated L, W, and θ values within the above specified ranges, are possible. However, it is generally preferable to limit the total number of electrodes to six or less.

It will be noted that in the embodiments illustrated in FIG. 22A–22C, 22G–22H, the electrodes 250 are guided by the shape of the sheath 248. That is, the electrodes can be directed towards or away from each other if the guide sheaths are angled towards or away from each other. Similarly, different θ values are possible if the sheaths are formed with the appropriately angled bends.

Figure 22:
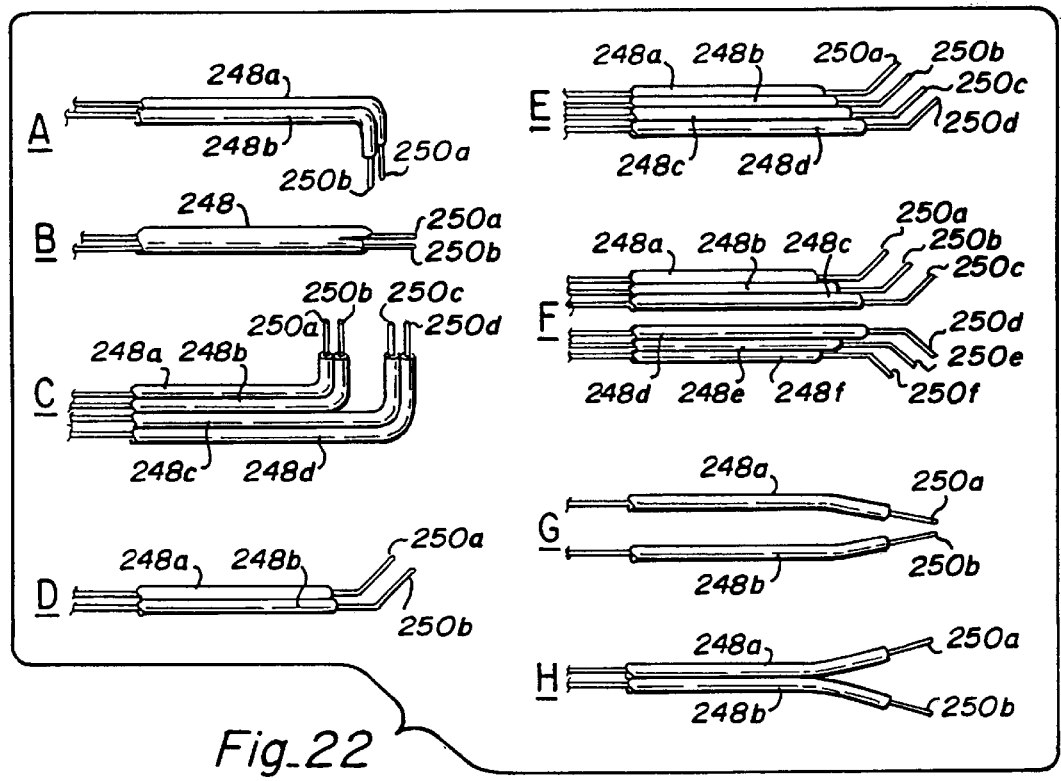
FIGS. 22A–22H illustrate alternate electrode configurations for the retractable electrode assembly shown in FIGS. 17 and 20.
Figure 23:
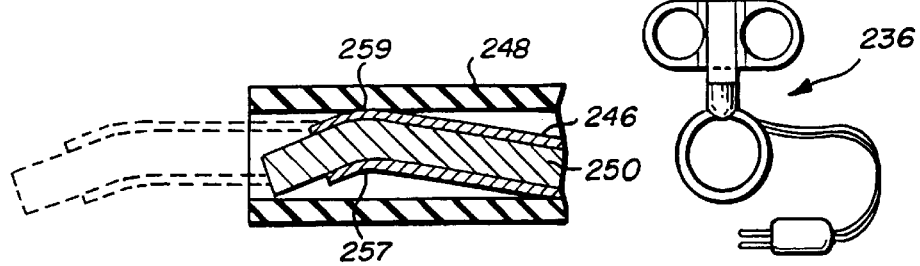
FIG. 23 is an enlarged view of the tip of the retractable electrode shown in FIGS. 22D–22F.

However, in the embodiments illustrated in FIG. 22D–22F, the sheaths are substantially straight and the electrodes themselves are bent in order to direct them in certain orientations. This feature is more clearly shown in FIG. 23 which illustrates a typical electrode having a bend formed at the location depicted by numeral 257. When the electrode is disposed within the sheath 248, the electrode 250 is in contact with at least one portion 259 of the inner surface of the sheath 248 because of the bend 257. When the electrode is extended beyond the sheath (shown in phantom lines), the electrode "flattens" within the sheath 248 while the electrode tip angles away from the sheath centerline in accordance with the bend 257 formed in the electrode.

Figure 24:
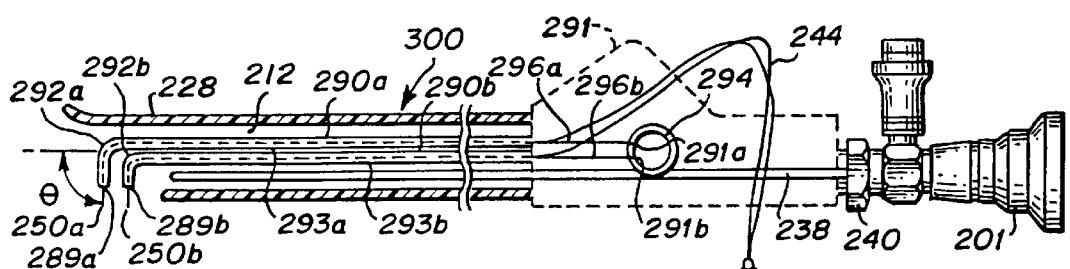
FIG. 24 is an alternate embodiment of the present invention including a retractable electrode assembly having a variable angle control mechanism.

FIG. 24 illustrates a retractable electrode surgical instrument 300 which is an alternate embodiment of the retractable electrode instrument 200 (FIG. 17). The instrument 300 includes many of the same elements as the instrument 200. These identical elements are identified with the same reference numeral as shown in FIG. 17. In this embodiment, each electrode 250a, 250b is enclosed within a bendable guiding sheath 290a, 290b. A guide wire 293a, 293b is disposed within each sheath 290a, 290b and includes a first end 289a, 289b and a second end 291a, 291b. Each first end 289 of each guide wire 293 is attached (e.g. welded or adhesively bonded) to an inner surface of a bendable or bellows portion 292 of the sheath 290 at a location proximate the open end of the sheath 290. Each second end 291 is attached to a lever or knob 294 which is mounted to an outer surface of a housing 291. The housing 291 is similar to the housing 232 and includes communication ports for an irrigation valve and an evacuation valve (neither shown). In operation, when there is no tension on the guide wires the sheaths are straight within the conduit, i.e. θ is 0 degrees. As the surgeon pulls back on the knob or lever, the wires are tensioned and the tips of each sheath is pulled back as illustrated until a desired θ value is obtained. In this embodiment, both the L and the θ values can be adjusted by the surgeon in situ.

Figure 25:
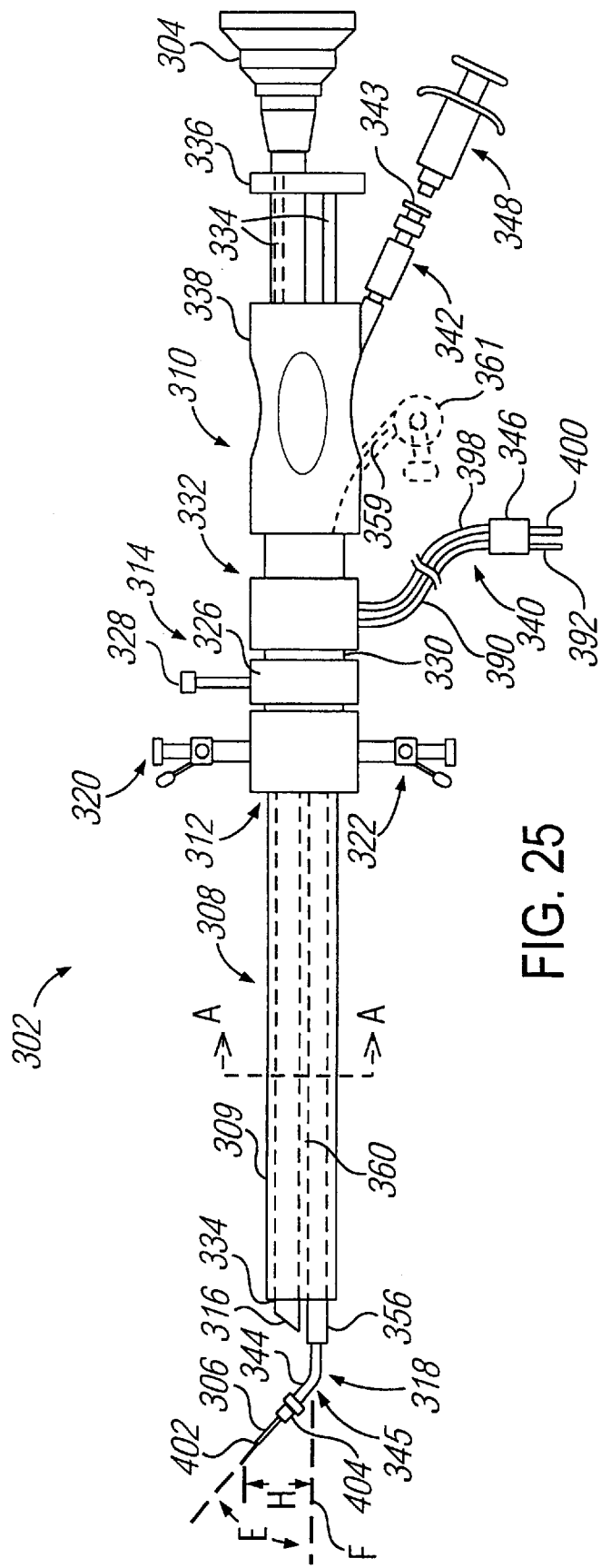
FIG. 25 shows an endoscopic surgical instrument assembly with a hollow core electrode.

Referring now to FIG. 25 of the drawing there is illustrated a further embodiment of the present invention including an endoscopic surgical instrument assembly 302 for inserting an endoscope 304 and a hollow core electrode/needle 306 into a patient's body. The assembly 302 further includes three major sub-assemblies including a housing 308, a treatment device assembly 310, and the endoscope 304.

The housing 308 has a probe 309 for insertion into the patient's body, an irrigation and evacuation block 312, and a housing connector 312. The housing 308 has a single access conduit with an annular opening 360 (see FIG. 26) therethrough for passage of an endoscope probe 316 and an electrode assembly 318. The block 312 includes an irrigation valve assembly 320 and an evacuation valve assembly 322. The irrigation valve assembly 320 is for passing irrigation fluid into the annular opening 360 and out the end 324, and the evacuation assembly 322 is for evacuation of irrigation fluids along with body materials suctioned into end 324 and out through the evacuation assembly 322.

The receptacle block 314 is shown to include a locking ring 326 and handle 328 for locking engagement with a plug 330 of the treatment device assembly 310. The details of a locking engagement are known to those skilled in the art, and many variations for locking the housing 308 to the apparatus 310 will be apparent, and they are included in the spirit of the present invention.

The assembly 310 includes the electrode/needle 306 and structure for supporting, extending and retracting it, as well as an apparatus for inserting liquids, optic fiber or tools through the hollow core of the needle/electrode into the body of a patient. An electrode/needle control structure for extending and retracting the electrode/needle includes a central portion 332 having guide bars 334 extending therefrom and terminating in an end block 336, and an RF power connector assembly 340 attached. thereto. A slidable portion 338 is coaxially and slidably mounted on the central portion 332 with the guide bars extending therethrough, and has attached thereto the electrode/needle assembly 318, and needle/electrode supply connector assembly 342. As an operator moves the slidable portion 310 relative to the central portion 332, the electrode/needle 306 is moved relative to the central portion 332, thereby providing the movement to extend or retract the electrode/needle. The connector assembly 340 connects through the portion 332 to the electrode 306. In monopolar operation, only pin 400 of connector 346 and line 398 are required in order to make contact with the electrode 306. Line 390 and pin 392 may be excluded for monopolar operation. As explained above, the electrical return path for monopolar operation is through a plate on the exterior of the patient's body. For bipolar operation, line 390 and pin 392 provide for connection from an electrically conductive guiding sheath/sleeve 344 (FIGS. 26, 27) to an electrical return line from an RF power supply.

The insertion of fluids, optic fibers and microsurgical instruments is accomplished through the assembly 342, which has an annular opening 343 providing access through slide portion 338 to an annular opening 350 (FIG. 26) of the hollow core electrode 306. The fluids, optic fibers such as laser fiberoptics and microsurgical instruments can be inserted through assembly 342 through the electrode 306 into the patient for treatment. A syringe 348 is shown representing a variety of devices which can mate with the assembly 342 for the insertion of fluids/chemical agents.

The slidable portion 338 is moveable back and forth along the guide rods 334 to extend or retract the electrode 306.

Figure 26:
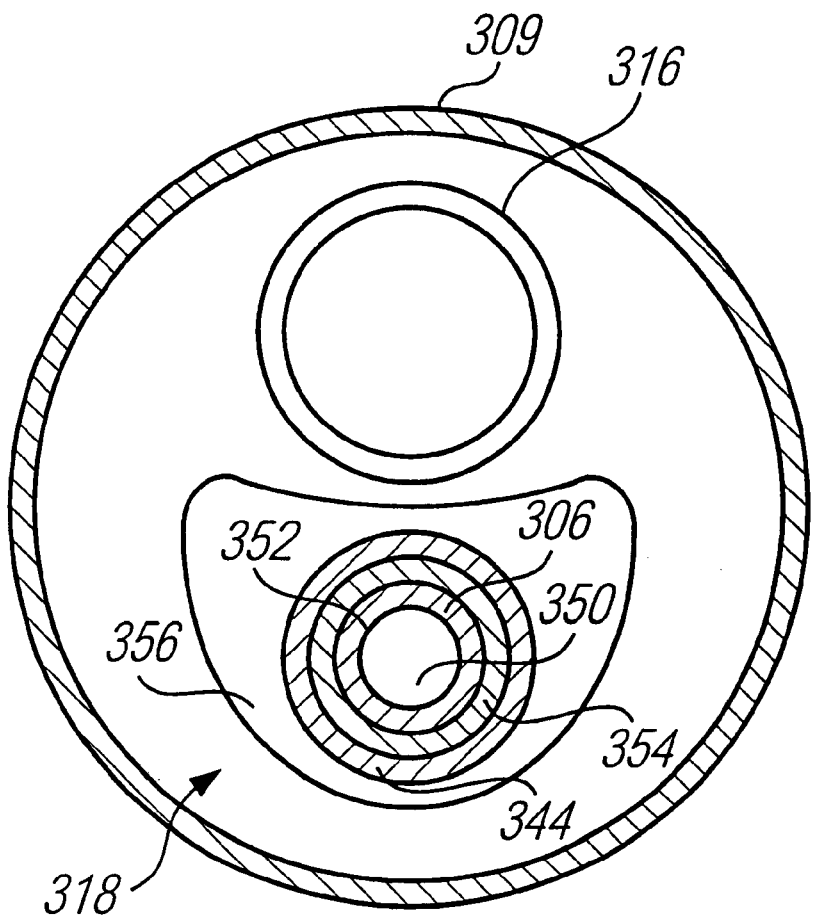
FIG. 26 shows a detailed cross section of the hollow core electrode, and a single access conduit and endoscope.

A cross sectional end view A-A of the assembly of FIG. 25 is shown in FIG. 26 for clarifying the electrode assembly 318, the probe 309 and endoscope probe 316. The electrode assembly 318 includes the electrode 306 with the annular opening 350. The electrode 306 has a wall 352 which is preferably constructed of nickel-titanium material. The electrode 306 slides within an electrically insulative material 354, which is further surrounded by a supportive structure including a sleeve 344 and support 356. The circular electrode cross section shown in FIG. 26 is the preferred embodiment and is given by way of example. Other electrode cross sections are also included in the spirit of the present invention, including square, triangular, oval, etc. shapes for the outer diameter and/or inner diameter of the hollow core electrode 306. The support 356 is used to guide the endoscope probe 316. The shape of support 356 is given by way of example, and other shapes and structure are included in the spirit of the present invention. The sleeve 344 and support 356 can be constructed from a variety of materials known to those skilled in the art. For monopolar operation, sleeve 344 and support 356 can be an integral structure of either insulative or conductive material. The support 356 is preferably insulative for bipolar operation and the sleeve must be conductive, serving as the return path for energy to the RF power supply. The shape of the support 356 is by way of example, and other shapes and structure will be apparent to those skilled in the art and are included in the present invention. The preferred material for the electrode 306 is nickel-titanium, although other materials with suitable resiliency and conductivity are included in the spirit of the present invention.

Referring again to FIG. 25, the angle "E" of the electrode 306 from the primary electrode axis "F" is an important feature of the present invention. This angle, in cooperation with the capability of extending and retracting the electrode, makes it possible to insert the electrode in body tissue located away from the axis "F". This is accomplished in the preferred embodiment wherein the sleeve 344 is rigid, providing guidance for the electrode 306, including the curved end 345 for directing the electrode at the angle "E". The height "H" of the sleeve 344 is designed to allow use with a variety of currently manufactured types of endoscopic housings such as 308. The retractable electrode feature of the present invention allows the electrode to be withdrawn into the sleeve 344 so that only a clearance "H" is required in the single access conduit in order to install the electrode assembly 318 through the housing opening 360. The preferred angle "E" is 70 degrees, although other angles from 0 to 360 degrees are also useful and included in the invention.

The angle "E" of the electrode is also controllable through use of the bendable guiding sheath 290 with bellows as explained in the above text referring to FIG. 24, and this type of electrode assembly is also useable with the device assembly 310 of FIG. 25. The details of incorporation of the guiding sheath 290, the guide wire 293 (FIG. 24), and controls to tension the guide wire to adjust the angle "E" will be understood by those skilled in the art from the disclosure relating to FIGS. 24–27. For example, in FIG. 25, the dashed line 359 indicates the passage of a guide wire from a sheath, such as guide wire 293 and sheath 290 of FIG. 24. The guide wire would pass through the slidable portion 310 and terminate in a wire tension control 361 as indicated in dashed outline.

The assembly of FIG. 25 is also illustrative of an apparatus for insertion of fluids, optic fibers, microsurgical instruments, etc. through the electrode 306 without the application of RF energy. In this case, the electrode will be termed more appropriately "needle" having a hollow core.

Figure 27:
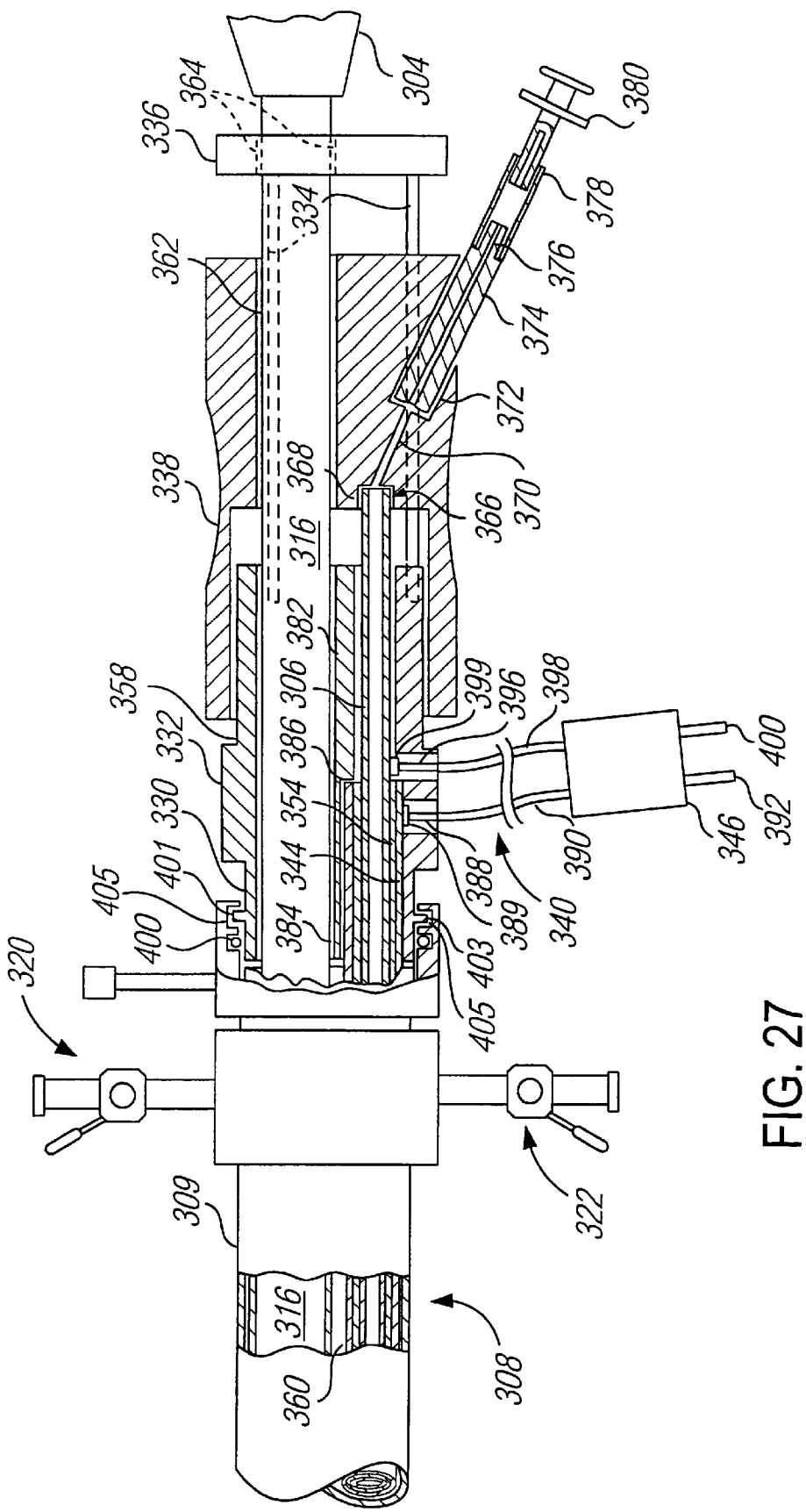
FIG. 27 shows further details of the assembly of FIG. 25.

The operation of the assembly 302 is further described in FIG. 27 which shows a preferred embodiment of the structure for moving the electrode and for the application of RF energy and insertion of fluids, etc. through the electrode/needle 306.

The stationary portion 332 has an annular opening 358 for passage of the endoscope probe 316 that extends through to the annular opening 360 in the probe 309, and through annular openings 362 and 364 in the sliding portion 338 and end block 336. The guide rods 334 are shown embedded in the stationary portion 332 and the end block 336. The sliding portion 338 is moved by the operator along the guide rods 334 to extend or retract the electrode 306. As shown, electrode 306 passes through stationary portion 332 and is secured at 366 in the bore 368. A second bore 370 extends from bore 368 to a larger bore 372 in which an adaptor 374 is secured having an end 376 for connection of a hose 378 connected to a plug 380.

The stationary portion 332 has a bore 382 for passage of the electrode 306. The insulative material 354 and sleeve 344 pass through a larger bore 384 ending at 386. In the case where bipolar operation is used, sleeve 344 must be conductive, and is electrically coupled to pin 388 which is connected to line 390 of connector assembly 340. The method of coupling the sleeve 344 to the pin 388 is shown to be capacitive, as indicated by plate 389. Other methods of coupling known to those skilled in the art are also included in the spirit of the present invention, including for example, spring loaded direct contact, weld/solder joint, etc.

In the case of monopolar operation, no electrical contact to the sleeve 344 is required and pin 388 and line 390 and the corresponding pin 392 of the connector 346 are unnecessary. The electrode 306 continues on through bore 382, and is shown coupled to a pin 396 connected to line 398 leading to pin 400 of connector 346. The contact of pin 396 to electrode 306 must allow for movement of the electrode. FIG. 27 shows an RF coupling as indicated by plate 399. Spring loaded contact mechanisms can also be used and are included in the invention.

In order to prevent leakage of irrigation and evacuation fluids from exiting around the housing connector 314, an "O" ring 400 is used, as shown mounted on the plug 330. The locking mechanism of ring 326 is indicated by pins 401 and 403 from plug 330 into corresponding grooves 405 of ring 326.

Referring again to FIG. 25, in operation the probe 309 of assembly 302 is inserted in the patient's body. The electrode 306 is then moved into contact with tissue by moving sliding portion 338. RF energy is applied to the electrode 306 through connector assembly 340. In monopolar mode, the RF energy vaporizes tissue near the electrode tip 402, and returns by way of a plate attached to the exterior of the patient's body. In bipolar mode, the active side of the RF power supply is connected to the electrode 306 through line 398 (FIG. 27) and the return side of the RF supply is connected to the sleeve 344 through line 390. The RF energy then vaporizes tissue near the tip 402 and the energy is returned by way of the sleeve 344, largely concentrated between the end 402 of the electrode and the end 404 of the sleeve 344. The benefit of bipolar operation, as discussed above, is that the damaging effects of RF energy are limited to the vicinity of the area under treatment.

A method of localized fluid therapy, preferably using the endoscopic instrument described above, is illustrated in FIG. 28. The probe 309 and needle (FIG. 25) are inserted into the patient's body (block 406, FIG. 28) through an appropriate opening, such as an incision, or through a natural passageway such as a urethra or cervical canal, etc. The hollow core needle is inserted through the probe either before or after insertion of the probe in the body. Through use of an endoscope, or non-invasive detection positioning and imaging methods, for example using ultrasound, etc., the user accurately positions the probe near a site to be treated. The apparatus of FIG. 25 includes the slidable portion 338, which is a preferred embodiment for extending and retracting the needle 306. The use of non-invasive detection and imaging methods with X-RAY, CT SCAN, MRI, ultrasound, fluoroscopy, etc. to monitor probe and needle placement in conjunction with, or without an endoscope, allows an instrument with a smaller probe 309 diameter to be used. The spirit of the present invention includes both alternatives. The needle assembly 318 can be solely for application or injection of fluid to a precise target tissue location, or it can be additionally for application of RF energy.

According to the method of the present invention, the needle 306 is used to apply fluid to a tissue surface, or is advanced into body tissue in need of treatment (block 410), the needle depth being observed by use of any of various imaging means, such as those listed including an endoscope, a scale on the injector 348 or probe handle, or noninvasive imaging and position detection using X-RAY, CT scan, fluoroscopy, ultrasound etc. As shown in FIG. 25, the needle 306 can extend at any angle relative to the axis of the probe in order to reach the target tissue. Treatment fluid is then injected (block 412) into the specific target area of tissue without affecting the surrounding area. The needle is then removed from the treatment site (block 414).

At this point the apparatus can be either removed, or a new site in need of treatment can be identified and therapy applied. The process of identification is indicated by block 416. In the case where an endoscope is used, with or without the aid of observation with X-RAY, CT scan, fluoroscopy or ultrasound, the probe can be moved to observe additional tissue to determine further areas in need of treatment. If observation is limited to X-RAY, CT scan, fluoroscopy, ultrasound, these tools are used alone to determine any additional targeted treatment areas. In either of the tool combinations noted above, they are used to precisely locate the targeted treatment area, place and/or insert the needle to the desired depth, and observe the fluid flow and effect on the tissue. If no further treatment is required, the probe 309, needle assembly, and endoscope (if present) are removed (block 418). If further treatment is required, the probe 309 and needle are positioned accordingly (block 410) and the needle is used to apply fluid to the tissue surface, or it is advanced into the tissue, and a sufficient volume of fluid is injected (block 412).

The present invention provides the method and apparatus for application of fluid to a localized targeted interior tissue surface, or to a similar localized targeted volume of tissue by injection. This is a significant advantage over prior art methods wherein fluid injection affects larger areas including the whole body.

According to the method of the present invention, the fluid can be of any kind for any purpose. A summary of preferred fluids is included in FIG. 29. A preferred embodiment includes the use of a necrossing agent for causing a localized death of tissue. Fluids that can be used for the purpose are listed in FIG. 29, and include ethanol alcohol (1% to 100%), saline solution (0.9% to 99%), acetic acid (1% to 100%), and natural extracts. In this case where the fluid is for the purpose of causing tissue death, the fluid is applied/injected at a rate to cause the tissue death in a localized targeted area without affecting surrounding tissue.

The necrossing agent can be combined with an anesthetic agent and/or with an antibiotic. Anesthetic agents, for example, include Lidocaine, Markaine and Sensorcaine as listed in FIG. 29, and other anesthetic agents known by those skilled in the art. Similarly, antibiotic agents include the various products known in the art. The fluids that can be used in accordance with the therapy of the present invention include mixtures of the above listed items and other chemicals, agents and their solutions in the form of liquid, gel, suspensions or semi-liquid that will be understood by those skilled in the art.

Figure 28:
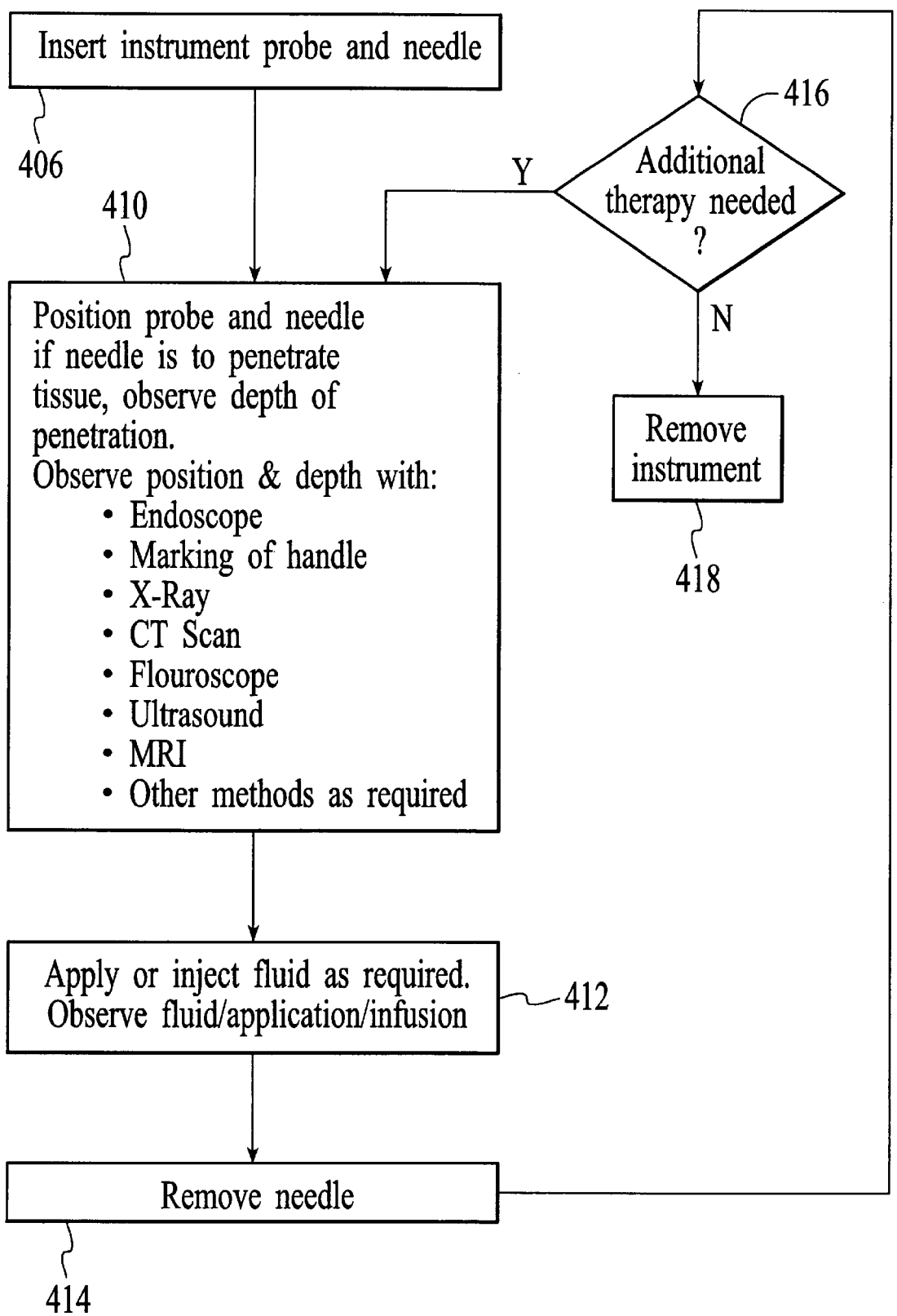
FIG. 28 is a flow chart illustrating the method of fluid therapy.

The method of FIG. 28 according to the present invention is meant to cover treatment of any body part. Preferred, embodiments of the present invention include treatment of uterine myoma, fibroids, ovarian cancer, bladder, and breast, tumors and cysts (benign or malignant), etc., and in the procedure of endometrial ablation of the uterine lining. An important embodiment in use with male patients is treatment of BPH (benign Prostatic Hyperplenia), enlarged prostate growth and prostate cancer. In this case, the probe is typically inserted transurethrally (through the male urethra) or transperineally with or without an incision.

Figure 30:
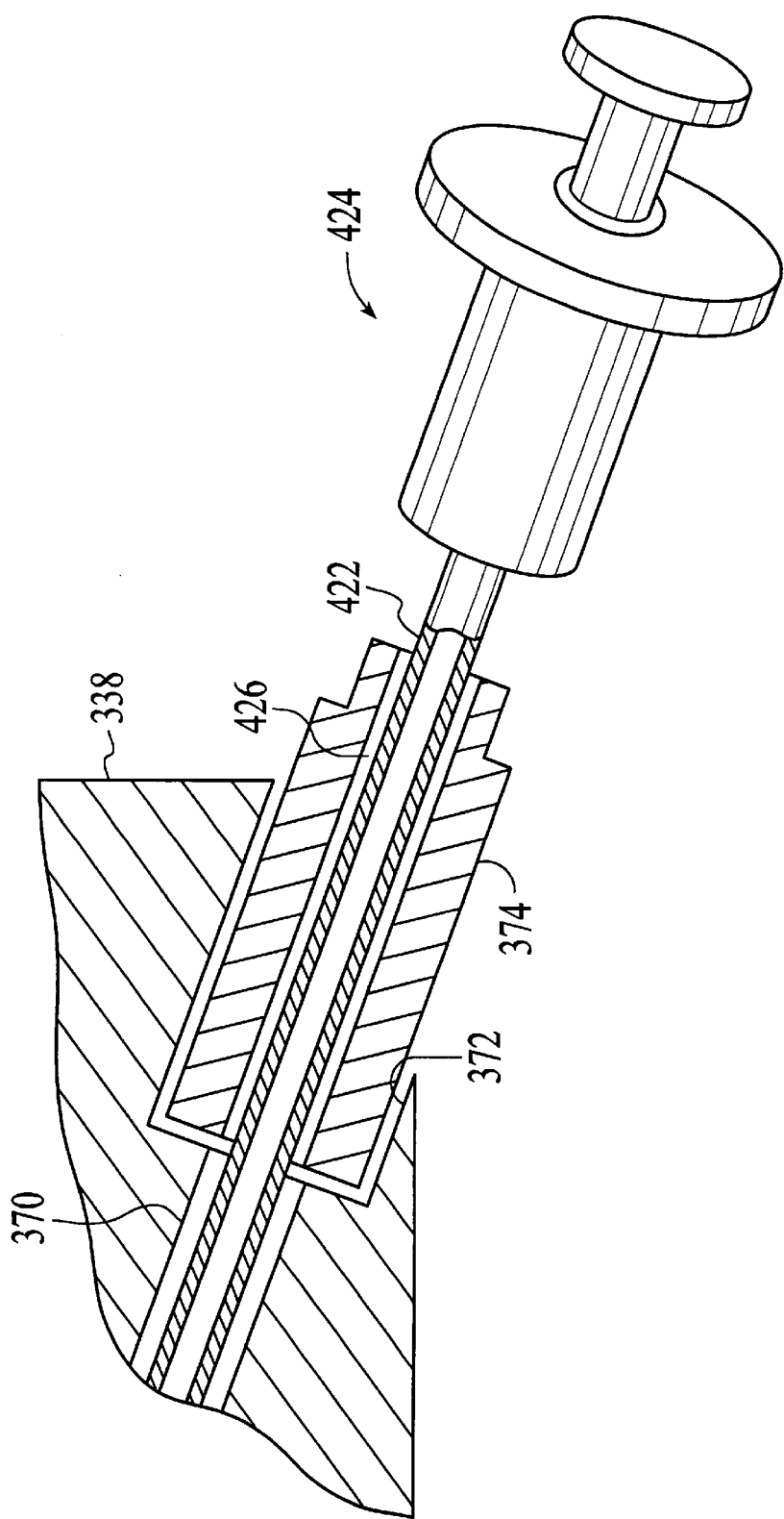
FIG. 30 illustrates an alternate apparatus for inserting a hollow needle through a probe.

A further embodiment of the fluid application/injection apparatus of FIGS. 25–27 is shown in FIG. 30, wherein instead of the conduit item 306 (needle) being in fact a needle, such as for insertion into tissue, it is simply a conduit through which a long resilient needle 422 (FIG. 29) is inserted for passage through the bore 426 of adapter 374, bore 370 and through the probe 309 for application of fluid to a tissue surface or insertion into body tissue, taking the place of needle 306 as shown having a tip 402 in FIG. 25. The needle 422 in FIG. 30 is shown attached to a fluid injector apparatus 424. Other apparatus for the injection of fluid into a needle known to those skilled in the art are also included in the spirit of the present invention.

Figure 31:
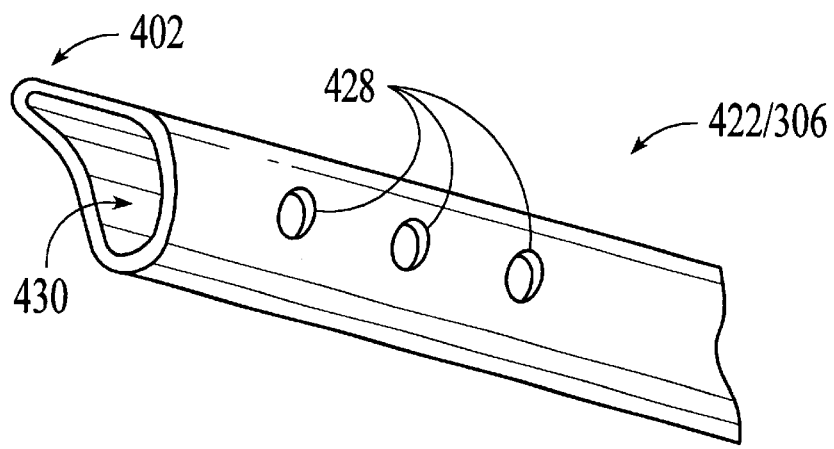
FIG. 31 shows the fluid delivery openings in a sharp or pointed needle.

The tip 402 of the needle, which can be either needle 306 as depicted in FIG. 25 or needle 422 of FIG. 30, can be configured as shown in FIG. 31, with or without holes 428 in the side of the needle 422/306 for dispensing of fluid in addition to hole 430 in the end of the needle. It should be noted that the needle can exit the probe at any angle, and can be either straight or curved. A needle having a portion that curves after exit from the probe or conduit is fabricated by constructing the needle from a resilient material that is pre-stressed in a curved shape. A preferred material is a nickel-titanium alloy. Curved needles of this type are shown as items 432–436 of FIG. 32A, illustrating their curved behavior after exiting the probe.

The invention also includes various combinations of the features of the apparatus of FIGS. 25–28 and 30. For example, although the apparatus as illustrated in FIGS. 25–28 and 30 includes electrode apparatus, endoscope apparatus, and fluid injection apparatus, the spirit of the invention includes a probe with the fluid injection/application apparatus alone, or with an endoscope and/or with the electrode apparatus or any combinations of these items. For example, if fluid injection/application capability is the only feature needed, the diameter probe 309 can be significantly reduced, easing entry into the body. These and other combinations that will be apparent to those skilled in the art are included in the spirit of the present invention.

Figure 32A:
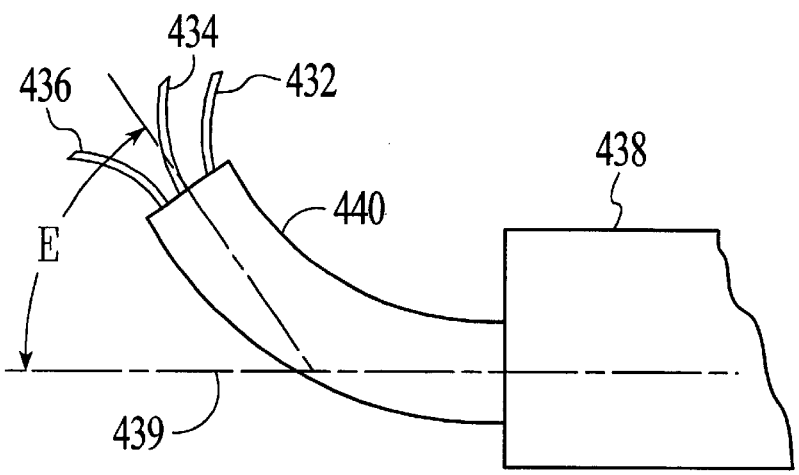
FIG. 32A illustrates multiple needles extending from and at an angle to an axis of a probe.
Figure 32B:
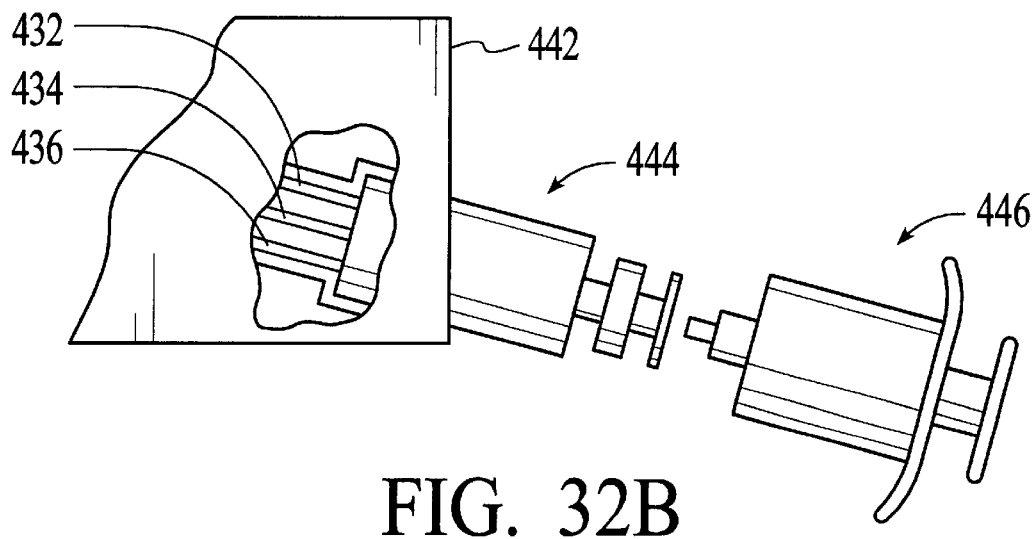
FIG. 32B shows apparatus for injection of fluid into multiple needles.

Referring to FIGS. 32A and 32B, the use of multiple hollow core needles 432, 434, 436 is illustrated. FIG. 32A shows a probe 438, similar to probe 309 of FIG. 25 except for having a sleeve 440, similar to sleeve 344, except with capacity for three needles 432, 434 and 436. The needles can exit at any angle "E" relative to the axis 439 of the probe 438, the specific angle "E" dependent on the bend of the sleeve 40. Although FIG. 32A shows three needles, any number of needles are included in the spirit of the invention. The needles 432, 434, 436 are extended and retracted in a similar manner as described above for a single needle. A preferred construction of the needles is from a resilient nickel-titanium alloy, and the needle being pre-stressed into a curved shape. FIG. 32B shows a slidable portion 442, similar to slidable portion 338 of FIG. 25, except configured to accommodate the multiple needles 432, 434, 436. Also shown is an assembly 444 for adapting the needles to a fluid injector 446, similar to injector 348 of FIG. 25.

A still further embodiment of the present invention includes insertion of a needle into a body directly without the use of a probe for guidance, either through a natural opening or through an incision, or by direct insertion using the sharp needle point to puncture/incise the tissue as the needle is inserted. The position of the needle in this case can be guided using ultrasound, MRI, CT scan, etc. The needle tip is guided to a position adjacent a target tissue surface for topical application of fluid, or is inserted into the target tissue/organ for injection of fluid.

Figure 33A:
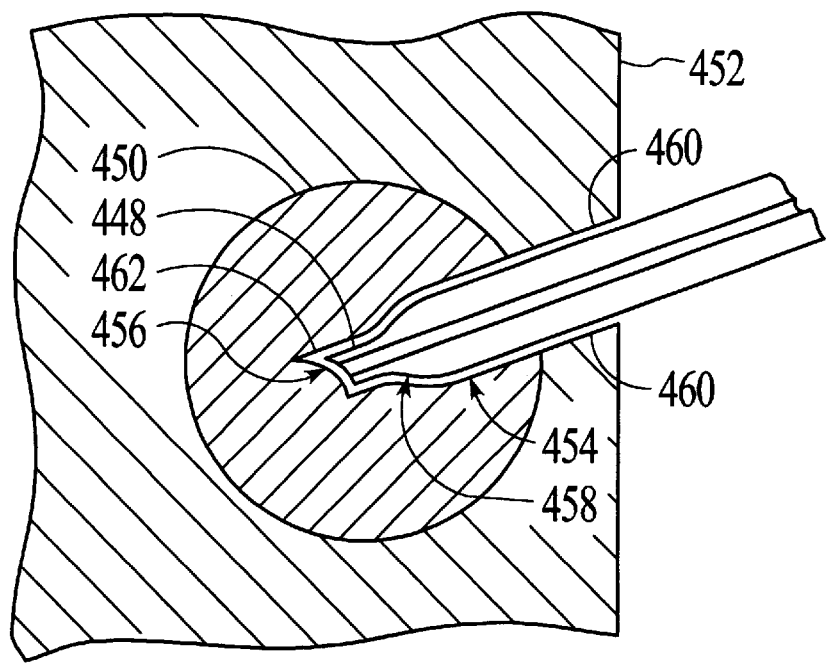
FIG. 33A illustrates use of a needle without a probe for fluid therapy.
Figure 33B:
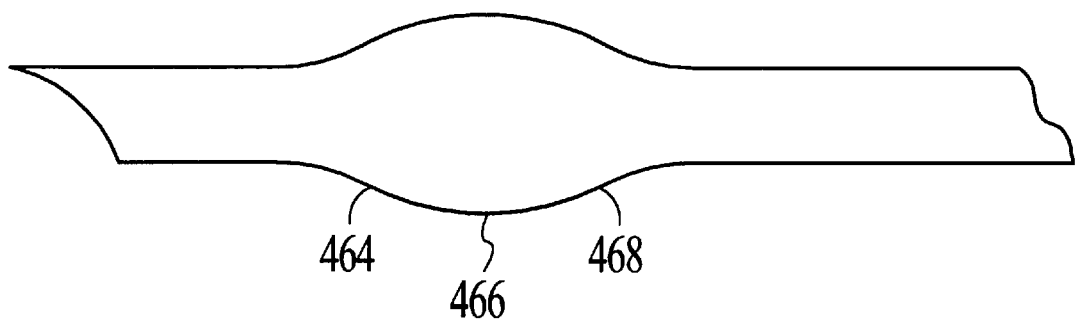
FIG. 33B shows a needle with a fluid block.

FIG. 33A is used to illustrate the insertion of a needle 448 in target tissue 450 inside a body 452 without the guidance of a probe as explained above, and also to illustrate the use of an enlargened section 454 behind a tip 456 of the needle 448. A tapered section 458 permits easier needle entry. The purpose of the enlargened section 454 is to provide a zone of increased contact between the tissue surface 460 in contract with the needle relative to the contact between the needle and tissue surface 462 near the needle tip. The increased contact is a result of the larger expansion of tissue, and the purpose is to provide a barrier to keep fluid exiting at the needle tip 456 from traveling back along the outside of the needle. This feature helps assure that the zone of treatment will be localized to the area immediately surrounding the needle tip. The needle 448 with enlargened region can be used in the embodiments described above in cooperation with a probe, etc. or it can be used by itself as illustrated in FIG. 33A. Other ways of constructing a fluid block to keep liquid from traveling back will be apparent to those skilled in the art after reading the disclosure, and these are included in the spirit of the present invention. For example, an abrupt increase in needle diameter in back of the tip will also work, or as shown in FIG. 33B, a taper 464 to a short area 466 and then a taper 468 back down again. The enlargened area can also be constructed from a separate, snug fitting sleeve over the needle.

Figure 34:
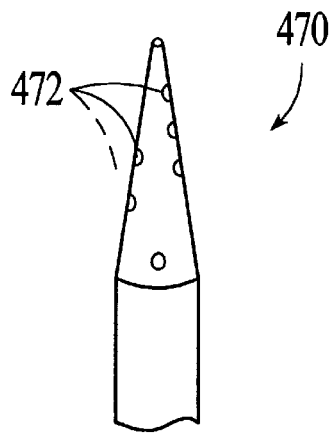
FIG. 34 shows a needle with a conical tip and fluid delivery holes.
Figure 35:
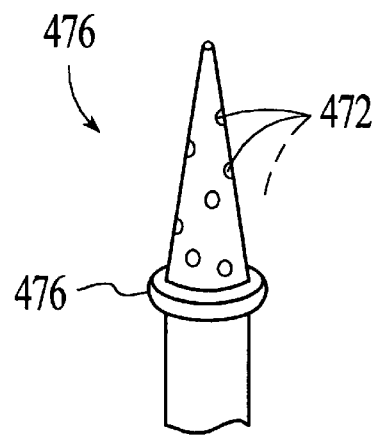
FIG. 35 shows a conical needle tip with a fluid block.
Figure 36A:
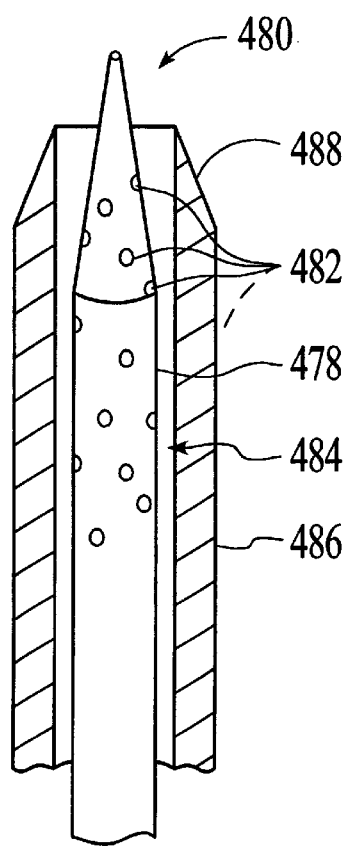
FIG. 36A illustrates a needle core with a plurality of delivery holes selected with a slidable sleeve.
Figure 36B:
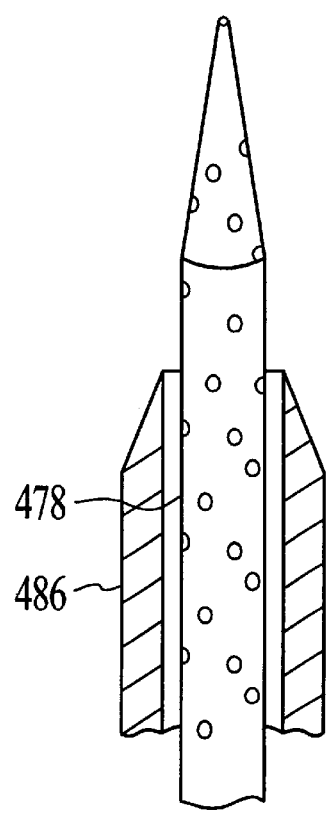
FIG. 36B shows the slidable sleeve in a second position for treating a larger area.

FIG. 34 shows a conically shaped needle tip 470 with fluid delivery holes 472. FIG. 35 shows a conical tip 474 similar to tip 470 but with an enlargened region 476 for blocking fluid. FIGS. 36A and 36B show a needle 478 with a conically tapered tip 480 and delivery holes 482 spaced along the conical tip 480 and a length of the non-conical portion 484. An adjustable sleeve 486 is shown with a tapered end 488 for ease of entry. The sleeve is a close fit over the needle, and is shown in FIG. 36A blocking all of the holes on the straight portion but allowing fluid to escape from the holes 482 in the tapered tip 480 due to the space between the sleeve and the tip. This position provides a minimal zone of fluid treatment. As the sleeve 486 is moved back, the zone of treatment is increased, as shown in FIG. 36B. The needle assembly of FIGS. 36A, 36B can be used alone with a fluid injector, similar to the illustration of FIG. 33A, or with the apparatus as shown in FIG. 25 or other compatible apparatus. Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A method for treating a localized portion of body tissue comprising:
   (a) inserting a means for delivering fluid into said body;
   (b) positioning said means for delivering fluid at a target tissue in need of treatment; and
   (c) applying fluid to said target tissue through said means for delivering fluid.

2. A method as recited in claim 1 wherein said applying includes depositing fluid on a surface of said tissue.

3. A method as recited in claim 1 wherein said applying includes penetrating said tissue to a desired depth with said means for delivering fluid.

4. A method as recited in claim 1 wherein said inserting includes inserting said means for delivering fluid through a natural opening in said body.

5. A method as recited in claim 1 wherein said inserting includes inserting said means for delivering fluid through an incision in said body.

6. A method as recited in claim 1 wherein said applying is restricted to a desired localized portion of tissue so as not to effect surrounding tissue.

7. A method as recited in claim 1 wherein said needle means includes a single hollow core needle.

8. A method as recited in claim 1 wherein said needle means includes a plurality of hollow core needles.

9. A method as recited in claim 1 wherein said fluid is a mixture of fluids.

10. A method as recited in claim 1 wherein said fluid includes a tissue necrossing agent.

11. A method as recited in claim 10 wherein said fluid further includes an anesthetic agent.

12. A method as recited in claim 10 wherein said fluid further includes an antibiotic.

13. A method as recited in claim 1 wherein said fluid is a mixture of a plurality of different fluids.

14. A method as recited in claim 1 wherein said fluid is a gel.

15. A method a recited in claim 1 wherein said fluid is a semi-liquid.

16. An apparatus for treating a targeted body tissue comprising;
   (a) a hollow core needle means; and
   (b) a probe for entering into said body, said probe having a canal means through which said needle means can be inserted, said needle means for applying fluid to said tissue.

17. An apparatus as recited in claim 16 wherein said needle means includes a hole in a sidewall for delivery of said fluid.

18. A method as recited in claim 16 wherein said needle apparatus includes a needle tip means at a distal end, needle apparatus having a treatment fluid delivery hole, and said needle apparatus having a fluid block for preventing fluid ejected from said fluid delivery hole from flowing between an outside of said needle apparatus and said tissue toward a proximal end of said needle apparatus.

19. A method as recited in claim 18 wherein said needle apparatus further includes a plurality of holes spaced along a length of said needle for delivery of said treatment fluid, and wherein said needle apparatus further includes a sleeve installed over said needle for selectively exposing a first plurality of said holes for controlling an area of tissue to be treated.

20. A method as recited in claim 1 wherein said adjusting includes guiding said needle apparatus with a guiding apparatus.

21. A method as recited in claim 20 wherein said guiding apparatus is an endoscope.

22. A method as recited in claim 20 wherein said guiding apparatus includes non-invasive detection positioning and imaging apparatus.

23. A method as recited in claim 1 wherein said inserting includes inserting said needle apparatus by puncturing said tissue.

24. An apparatus for treating a targeted body tissue comprising:
   (a) a needle apparatus including a hollow core needle for delivery of a treatment fluid to said targeted body tissue for treatment of said tissue;
   (b) a probe for entering into said body, said probe having a canal through which said needle apparatus can be inserted; and
   (c) adjustment apparatus for extending a distal end of said hollow core needle to a position beyond a distal end of said probe to said targeted tissue for deposition of said treatment fluid.

25. An apparatus as recited in claim 24 wherein said needle apparatus includes a hole in a sidewall for delivery of said treatment fluid.

26. An apparatus as recited in claim 24 wherein said needle apparatus includes a plurality of needles.

27. An apparatus as recited in claim 24 wherein said needle apparatus includes one or more needles constructed of resilient material pre-stressed in a curved shape.

28. An apparatus for treating a targeted body tissue comprising:
   needle apparatus including a hollow core needle for penetrating a targeted body tissue, said hollow core needle having a treatment fluid delivery hole, and said needle apparatus having a fluid block for preventing fluid ejected from said fluid delivery hole near the distal end of said hollow core needle from flowing between the outside of said needle apparatus and said tissue toward the proximal end of said needle apparatus, wherein said needle apparatus further includes a plurality of holes spaced along a length of said hollow core needle for delivery of said treatment fluid, and wherein said fluid block includes a sleeve installed over said hollow core needle for selectively exposing a first quantity of said holes for controlling an area of tissue to be treated.

* * * * *

UNITED STATES PATENT AND TRADEMARK OFFICE
CERTIFICATE OF CORRECTION

PATENT NO. : 6,231,591 B1
DATED : May 15, 2001
INVENTOR(S) : Desai

It is certified that error appears in the above-identified patent and that said Letters Patent is hereby corrected as shown below:

Column 23,
Line 4, reading "body tissue" should read -- target tissue in a body --;
Line 6, reading "a means for delivering fluid into said body" should read -- into said body a needle assembly through a probe apparatus, said needle assembly including a hollow core needle for delivering treatment fluid to a localized portion of target tissue of said body --;
Lines 7-8, reading "positioning said means for delivering fluid at a target tissue in need of treatment" should read -- adjusting a distal portion of said needle assembly, including said needle, to a position beyond a distal end of said probe apparatus for delivering treatment fluid to the target tissue in need of treatment --;
Line 9, reading "applying fluid" should read -- applying treatment fluid --;
Lines 9-10, reading "means for delivering fluid" should read -- needle --;
Line 12, reading "depositing fluid" should read -- depositing treatment fluid --;
Lines 15, 17 and 20, reading "means for delivering fluid" should read -- needle assembly --;
Lines 26 and 28, reading "means" should read -- assembly --;
Lines 29, 31, 33, 35, 37, 39 and 41, reading "said fluid" should read -- said treatment fluid --;
Lines 43-49, replace language of entire claim 16 with -- A method as recited in claim 1 wherein said needle apparatus includes a needle having a hollow core. --;
Lines 50-52, replace language of entire claim 17 with -- A method as recited in claim 16 wherein said probe includes apparatus for guiding said needle apparatus. --.

Column 24,
Line 41, reading "needle apparatus" should read -- a needle apparatus --.

Signed and Sealed this

Second Day of July, 2002

*Attest:*

JAMES E. ROGAN
*Attesting Officer*  *Director of the United States Patent and Trademark Office*